(12) United States Patent
Kondo

(10) Patent No.: US 8,101,084 B2
(45) Date of Patent: Jan. 24, 2012

(54) PERCHLORATE ION TRAPPING AGENT

(75) Inventor: Mitsuru Kondo, Shizuoka (JP)

(73) Assignee: National University Corporation Shizuoka University, Shizuoka-shi (JP)

( * ) Notice: Subject to any disclaimer, the term of this patent is extended or adjusted under 35 U.S.C. 154(b) by 456 days.

(21) Appl. No.: 12/439,997

(22) PCT Filed: Sep. 4, 2007

(86) PCT No.: PCT/JP2007/067223
§ 371 (c)(1),
(2), (4) Date: Mar. 4, 2009

(87) PCT Pub. No.: WO2008/029804
PCT Pub. Date: Mar. 13, 2008

(65) Prior Publication Data
US 2010/0200508 A1    Aug. 12, 2010

(30) Foreign Application Priority Data
Sep. 6, 2006   (JP) ................................. 2006-241297

(51) Int. Cl.
| | |
|---|---|
| *B01D 15/00* | (2006.01) |
| *B01J 39/00* | (2006.01) |
| *C02F 1/42* | (2006.01) |
| *G21F 9/04* | (2006.01) |
| *C07F 15/00* | (2006.01) |
| *C07D 403/02* | (2006.01) |
| *C07D 231/00* | (2006.01) |
| *C07D 231/02* | (2006.01) |
| *C07D 403/12* | (2006.01) |
| *C10L 1/16* | (2006.01) |
| *C10L 5/00* | (2006.01) |
| *C10M 101/02* | (2006.01) |
| *C10M 107/00* | (2006.01) |
| *C10M 143/00* | (2006.01) |
| *C10M 165/00* | (2006.01) |
| *C10M 167/00* | (2006.01) |
| *C10M 169/00* | (2006.01) |
| *C10M 171/00* | (2006.01) |

(52) U.S. Cl. ..... 210/683; 210/666; 210/681; 548/312.4; 548/313.7; 548/101; 585/11

(58) Field of Classification Search .................. 210/683, 210/666, 681; 548/312.4, 313.7, 101; 585/11
See application file for complete search history.

(56) References Cited

U.S. PATENT DOCUMENTS

| | | | |
|---|---|---|---|
| 3,565,837 | A | 2/1971 | Drawert et al. |
| 5,382,265 | A | 1/1995 | Mower |
| 2004/0256597 | A1 | 12/2004 | Barrett et al. |

FOREIGN PATENT DOCUMENTS

| | | |
|---|---|---|
| DE | 1745447 | 9/1971 |
| JP | 48-48615 | 7/1973 |
| JP | 95-04472 | 5/1997 |
| JP | 2004-346299 | 12/2004 |

OTHER PUBLICATIONS

Shen et al., 1999, "Synthesis and Characterization of Copper(II), Iron(II, Cobalt(II), Nickel(II), and Manganese(II) Complexes of Azido-1,4-Bis(Imidazol-1-YI-Methyl)Benzene (bix) or 1,4-Bis(Imidazol-L-YI-Methyl)-2,5-Dimethyl)Benzene (Mebix))".*

Cheng-Yong et al., 2001, "Coordination-directed assembly of trigonal and tetragonal molecular boxes Encapsulating anionic guests".*

Hartshorn et al., "Poly (9pyrazol-1-ylmethyl) benzenes: New Multidentate Ligands," *Aust. J. Chem.*, 48:1587-1599 (1995).

Kosaka et al., "Study on Perchlorate ions in Watershed Areas of the Tone River using IC/MS/MS," *J. of the Society of Environmental Instrumentation Control and Automation*, 11:215-218 (2006).

"System for Eliminating Perchlorate Salt that Supports Identification of Sources of Contamination," NEDO Foreign Report, No. 946 (2004).

Mihele et al., "AcȚiunea Unor Noi DerivaȚ Ai Imidazolil-Xilenilor Şi 3,5-Dimetil-Pirazolil-Xilenilor Asupra ActivităȚȚȚsecretorii Gastrice Şi A Motilităii Intestinale," *Farmacia*, 48:51-56 (2000).

Sato et al., "Size Selective Recognition of Anions by a Tetracationic Imidazoliophane," *Heterocycles*, 60:779-784 (2003).

Shen et al., "Synthesis and Characterization of Copper(II), Iron(II),

Perchlorate ion

Cobalt(II), Nickel(II) and Manganese (II) Complexes of Azido-1,4-Bis(Imidazol-1-YL-Methyl) Benzene (BIX) or 1,4-Bis(Imidazol-1-YL-Methyl)-2,5-Dimethyl-Benzene) (Mebix)," *Synth. React. Inorg. Met.-Org.Chem*, 29:1331-1338 (1999).

Su et al., "Ligand-Directed Molecular Architectures: Self-Assembly of Two-Dimensional Rectangular Metallacycles and Three-Dimensional Trigonal or Tetragonal Prisms," *J. Am. Chem. Soc.*, 125:8595-8613 (2003).

Gao et al., "Coordination Networks with Fluorinated Backbones," *Inorganic Chem.*, 45:1150-1155 (2006).

International Search Report for PCT/JP2007/067223 dated Dec. 11, 2007.

Baker et al., "Rapid Communication. Imidazolium-Linked Cyclophanes," *Aust. J. Chem.*, 52:823-825 (1999).

European Examination Report for Application No. 07806678.4, dated Nov. 8, 2010.

Eurosean Search Reeort for Application No. 07806678.4, dated Feb. 11, 2010.

Su et al., "Coordination-directed Assembly of Trigonal and Tetragonal Molecular Boxes Encapsulating Anionic Guests," *J. Chem. Soc., Dalton Trans.*, pp. 359-361 2001.

\* cited by examiner

*Primary Examiner* — Nam Nguyen
*Assistant Examiner* — Nader Hossaini
(74) *Attorney, Agent, or Firm* — Marshall, Gerstein & Borun LLP

(57) ABSTRACT

The invention provides a heterocycle-substituted aromatic compound represented by the following Formula (I). In Formula (I), one of $R^2$, $R^3$, and $R^4$ is $R^y$ at a meta- or para-position with respect to $R^x$, $R^1$, $R^2$, $R^3$, $R^4$ and $R^5$ not including $R^y$ each independently representing a hydrogen atom, a substituted or unsubstituted aliphatic group having 1 to 30 carbon atoms, or a sulfonate group, where $R^1$, $R^2$, $R^3$, $R^4$ and $R^5$ not including $R^y$ are not hydrogen atoms all together; $R^x$ and $R^y$ each independently represent the following heterocyclic substituent, $R^6$ and $R^7$ in the heterocyclic substituents each independently representing a hydrogen atom or methyl group, and A representing a five-membered or six-membered heterocyclic group containing at least one nitrogen atom.

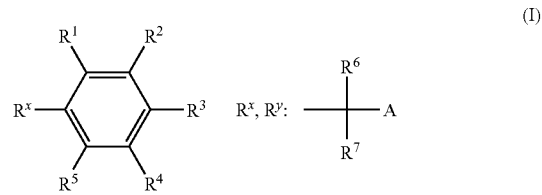

13 Claims, 9 Drawing Sheets

Perchlorate ion

PERCHLORATE ION TRAPPING AGENT

TECHNICAL FIELD

The present invention relates to a perchlorate ion trapping agent.

BACKGROUND OF THE INVENTION

Perchlorate salts are substances that affect the thyroid gland, which controls metabolic functions of adults and also promotes body growth of children. In recent years, a series of cases have been reported in which perchlorate ions have been detected at high concentrations in soil or water. Further, since the perchlorate ion ($ClO_4^-$) exhibits high solubility in water and is one of the anions that are least likely to interact with a cation, it is difficult to recover perchlorate ions from an aqueous solution as a precipitate or the like. In consideration of the influence of perchlorate ion on tap water, surveys on the concentration of perchlorate ions in rivers have recently been conducted (see, for example, the Journal of the Society of Environmental Instrumentation Control and Automation (EICA), 2006, Vol.11, No. 3, p. 215-218).

As a technique of eliminating a perchlorate salt from a liquid waste contaminated by the perchlorate salt (or perchlorate ions), a method of concentrating a perchlorate salt solution and adding KCl to the concentrated perchlorate salt solution to generate potassium perchlorate ($KClO_4$), then cooling the resultant to crystallize potassium perchlorate, is known (see, for example, Japanese Patent Application Laid-Open (JP-A) No. 9-504472). Further, a water treatment system for eliminating a perchlorate salt using a resin is known (see, for example, JP-A No. 2004-346299 and "NEDO Foreign Report, No. 946, 2004. 12. 15).

Further, compounds that form a capsule so as to enclose ions of various kinds are known (see, for example, J. Am. Chem. Soc., 2003, Vol. 125, No. 28, p. 8595-8613). Such a compound has a structure capable of readily forming a capsule backbone irrespective of the type or size of the ion to be incorporated in the capsule.

DISCLOSURE OF THE INVENTION

Problem to be Solved by the Invention

However, since the above method of generating and crystallizing potassium perchlorate from a perchlorate salt includes a step of concentrating a solution to evaporate a solvent therefrom; it is not possible to trap a perchlorate ion in the solution while maintaining the state of the solution. Further, in the above method of eliminating a perchlorate salt using a resin, there are problems such as the high cost of regeneration of the resin or poor selectivity in trapping the perchlorate ion. Further, even when elimination of perchlorate ions is attempted using the above compound capable of forming a capsule, it is not possible to selectively trap the perchlorate ion in a system including plural kinds of anion.

In view of the above, it is an object of the present invention to provide: an aromatic compound substituted by a heterocyclic group, the compound being capable of trapping a perchlorate ion in a liquid sample with high selectivity and efficiency; a coordination compound; a perchlorate ion trapping agent; a method of trapping a perchlorate ion; and a method of eliminating a perchlorate ion.

Means for Solving the Problem

The means for addressing the above subject are as follows.

<1> A heterocycle-substituted aromatic compound represented by the following Formula (1):

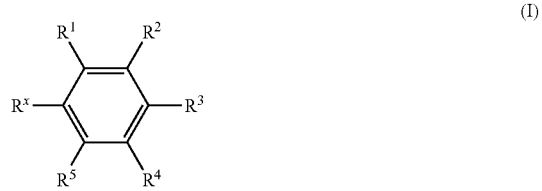

wherein in Formula (1), one of $R^2$, $R^3$ and $R^4$ is $R^y$ at a meta- or para-position with respect to $R^x$; $R^1$, $R^2$, $R^3$, $R^4$ and $R^5$ not including $R^y$ each independently represent a hydrogen atom, a substituted or unsubstituted aliphatic group having 1 to 30 carbon atoms, or a sulfonate group, where $R^1$, $R^2$, $R^3$, $R^4$ and $R^5$ not including $R^y$ are not hydrogen atoms all together; and $R^x$ and $R^y$ each independently represent the following heterocyclic substituent:

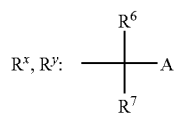

wherein in the heterocyclic substituent, $R^6$ and $R^7$ each independently represent a hydrogen atom or a methyl group, and A represents a five-membered or six-membered heterocyclic group containing at least one nitrogen atom.

<2> The heterocycle-substituted aromatic compound according to <1>, wherein $R^y$ is at a para-position with respect to $R^x$.

<3> The heterocycle-substituted aromatic compound according to <1>, wherein each of $R^6$ and $R^7$ are a hydrogen atom.

<4> The heterocycle-substituted aromatic compound according to <1>, wherein the aliphatic group has 1 to 10 carbon atoms.

<5> A heterocycle-substituted aromatic compound represented by the following Formula (II):

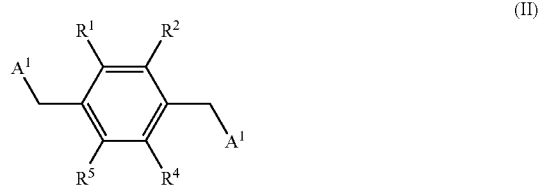

wherein in Formula (II), $R^1$, $R^2$, $R^4$ and $R^5$ each independently represent a hydrogen atom, a substituted or unsubstituted aliphatic group having 1 to 30 carbon atoms, or a sulfonate group, where $R^1$, $R^2$, $R^4$ and $R^5$ are not hydrogen atoms all together; and each $A^1$ represents a five-membered or six-membered heterocyclic group containing at least one nitrogen atom.

<6> A heterocycle-substituted aromatic compound represented by the following Formula (a):

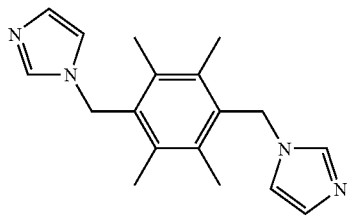

(a)

<7> A coordination compound comprising the heterocycle-substituted aromatic compound according to any one of <1> to <6>, and a metal ion capable of planar tetra-coordination or octahedral coordination.

<8> The coordination compound according to <7>, wherein the metal ion is at least one of $Zn^{2+}$, $Cu^{2+}$, $Ni^{2+}$, $Co^{2+}$, $Fe^{2+}$, $Mn^{2+}$, $Ag^+$, $Pd^{2+}$, or $Pt^{2+}$.

<9> A perchlorate ion trapping agent comprising a heterocycle-substituted aromatic compound represented by the following Formula (I):

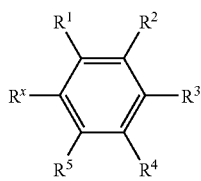

(I)

wherein in Formula (1), one of $R^2$, $R^3$ and $R^4$ is $R^y$ at a meta- or para-position with respect to $R^x$; $R^1$, $R^2$, $R^3$, $R^4$ and $R^5$ not including $R^y$ each independently represent a hydrogen atom, a substituted or unsubstituted aliphatic group having 1 to 30 carbon atoms, or a sulfonate group, where $R^1$, $R^2$, $R^3$, $R^4$ and $R^5$ not including $R^y$ are not hydrogen atoms all together; and $R^x$ and $R^y$ each independently represent the following heterocyclic substituent:

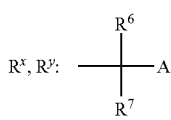

wherein in the heterocyclic substituent, $R^6$ and $R^7$ each independently represent a hydrogen atom or a methyl group, and A represents a five-membered or six-membered heterocyclic group containing at least one nitrogen atom.

<10> The perchlorate ion trapping agent according to <9>, wherein $R^y$ is at a para-position with respect to $R^x$.

<11> The perchlorate ion trapping agent according to <9>, wherein each of $R^6$ and $R^7$ are a hydrogen atom.

<12> The perchlorate ion trapping agent according to <9>, wherein the aliphatic group has 1 to 10 carbon atoms.

<13> A perchlorate ion trapping agent comprising a heterocycle-substituted aromatic compound represented by the following Formula (II):

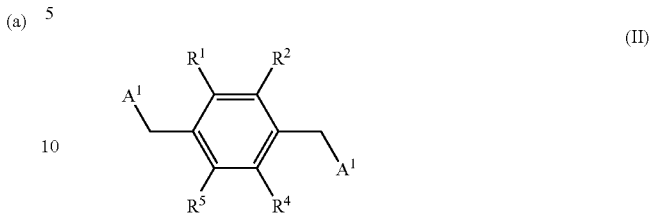

(II)

wherein in Formula (II), $R^1$, $R^2$, $R^4$ and $R^5$ each independently represent a hydrogen atom, a substituted or unsubstituted aliphatic group having 1 to 30 carbon atoms, or a sulfonate group, where $R^1$, $R^2$, $R^4$ and $R^5$ are not hydrogen atoms all together; and each $A^1$ represents a five-membered or six-membered heterocyclic group containing at least one nitrogen atom.

<14> A perchlorate ion trapping agent comprising a heterocycle-substituted aromatic compound represented by the following formula (a):

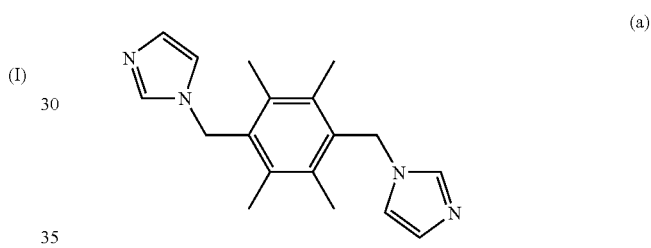

(a)

<15> The perchlorate ion trapping agent according to any one of <9> to <14>, further comprising a metal ion capable of planar tetra-coordination or octahedral coordination.

<16> A perchlorate ion trapping agent according to <15>, comprising the coordination compound according to <7> or <8>, wherein the metal ion is included as a part of the coordination compound.

<17> The perchlorate ion trapping agent according to <15>, wherein the metal ion is included as a part of a salt.

<18> The perchlorate ion trapping agent according to any one of <15> to <17>, wherein the metal ion is at least one of $Zn^{2+}$, $Cu^{2+}$, $Ni^{2+}$, $Co^{2+}$, $Fe^{2+}$, $Mn^{2+}$, $Ag^+$, $Pd^{2+}$, or $Pt^{2+}$.

<19> A method of trapping a perchlorate ion in a liquid sample, comprising a trapping step of bringing the heterocycle-substituted aromatic compound according to any one of claims 1 to 6, a metal ion capable of planar tetra-coordination or octahedral coordination, and the liquid sample into contact with each other to form a molecular capsule in which a perchlorate ion is trapped.

<20> A method of eliminating a perchlorate ion from a liquid sample, comprising:

a trapping step of bringing the heterocycle-substituted aromatic compound according to any one of claims 1 to 6, a metal ion capable of planar tetra-coordination or octahedral coordination, and the liquid sample into contact with each other to form a molecular capsule in which a perchlorate ions is trapped; and an elimination step of precipitating and eliminating the molecular capsule from the liquid sample.

Effects of the Invention

According to the present invention, it is possible to provide an aromatic compound with a heterocyclic substituent, the compound being capable of trapping a perchlorate ion in a liquid sample with high selectivity and efficiency; a coordination compound; a perchlorate ion trapping agent; a process of trapping a perchlorate ion; and a process of eliminating a perchlorate ion.

BEST MODE FOR CARRYING OUT THE INVENTION

<Aromatic Compound with a Heterocyclic Substituent>

Figure 1:
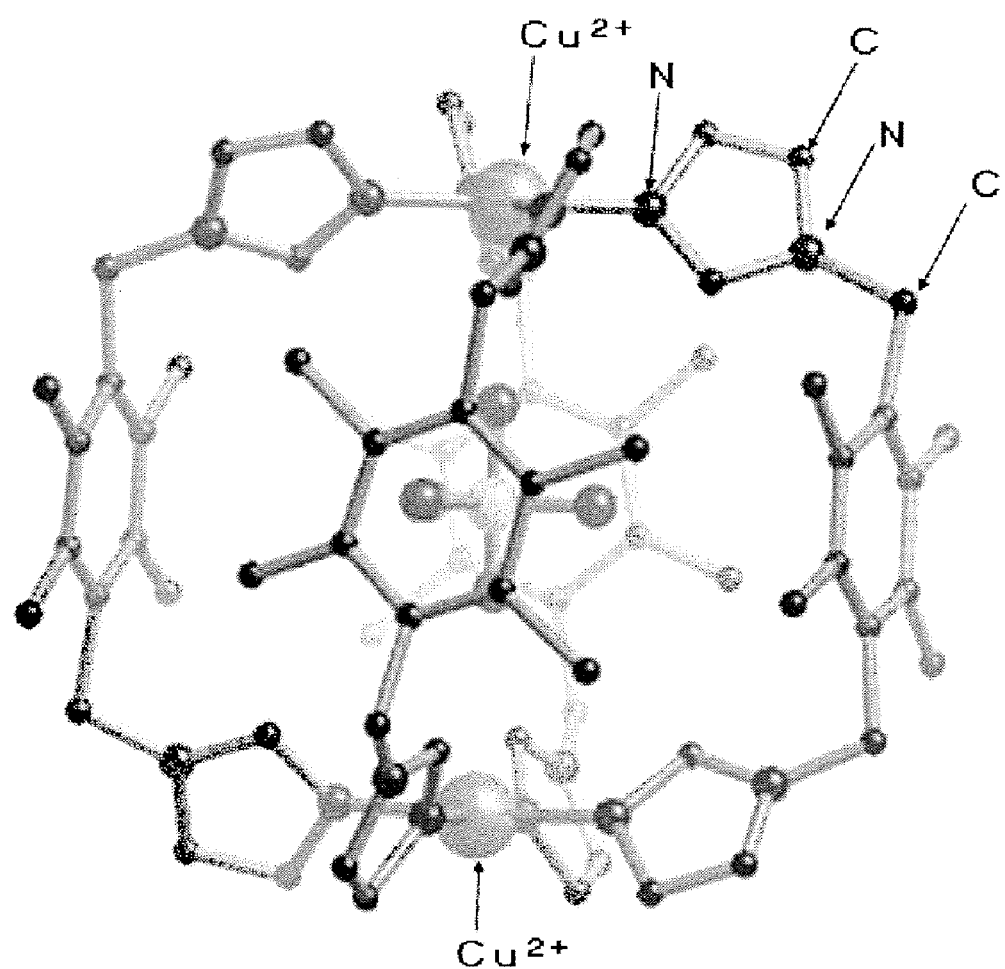
FIG. 1 is an image of the molecular capsule according to the present invention enclosing a molecule of perchlorate ion ($ClO_4^-$) without respect to the atomic radius.

The heterocycle-substituted aromatic compound according to the present invention is represented by the following Formula (I).

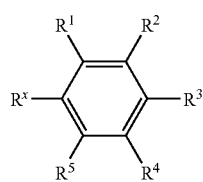

(I)

In Formula (1), one of $R^2$, $R^3$ and $R^4$ is $R^y$ that is at the meta- or para-position with respect to $R^x$, and $R^x$ and $R^y$ each independently represent the following heterocyclic substituent:

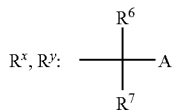

In Formula (1), $R^1$, $R^2$, $R^3$, $R^4$ and $R^5$ not including $R^y$ each independently represent a hydrogen atom, a substituted or unsubstituted aliphatic group having 1 to 30 carbon atoms, or a sulfonate group, where $R^1$, $R^2$, $R^3$, $R^4$ and $R^5$ not including $R^y$ are not hydrogen atoms all together; $R^6$ and $R^7$ in the heterocyclic substituent each independently represent a hydrogen atom or a methyl group; and A represents a five-membered or six-membered heterocyclic group containing at least one nitrogen atom.

When the heterocycle-substituted aromatic compound according to the invention contacts a metal ion capable of planar tetra-coordination or octahedral coordination and a specific anion in a liquid sample, a plural number of heterocycle-substituted aromatic compound assemble to form a capsule molecule together with the metal ion (self-assembly reaction), including the specific anion in the capsule molecule. In the invention, the capsular molecule including an anion is referred to as a "molecular capsule".

In the molecular capsule, the above compound and the metal ion form a space of 6.5 angstroms (0.65 nm)×6.5 angstroms (0.65 nm)×5.0 angstroms (0.50 nm). Therefore, only anions having the size of not more than the above space can be included in the molecule. Examples of such anions include a perchlorate ion ($ClO_4^-$) and a tetrafluoroborate ion ($BF_4^-$). In particular, the perchlorate ion can be selectively incorporated and does not readily detach from the molecule because of its size almost equal to the above space.

Consequently, the compound of the invention can trap a perchlorate ion not only with high selectivity but also in a reliable manner, because the compound does not allow the perchlorate ion to easily detach therefrom. Incidentally, the compound of the invention easily forms a polymeric structure with respect to an anion of other kinds, rather than forming a molecular capsule as described above.

Since the self-assembly reaction of the compound of the invention exhibits an extremely high selectivity with respect to a perchlorate ion, it is possible to trap the perchlorate ion in a highly efficient and reliable manner when the perchlorate ions exists in a liquid.

From the viewpoint of forming a trapping space having no gap so that a perchlorate ion does not detach therefrom, it is preferable that $R^y$ is at the para-position with respect to $R^x$, namely, $R^3$ is $R^y$.

From the viewpoint of regulating the number of types of isomers of the generated molecular capsule to facilitate the identification of the resulting product, it is preferable that $R^y$ and $R^x$ are the same kind of heterocyclic substituent.

From the viewpoint of forming a molecular capsule without causing steric hindrance with other substituents of the aromatic ring, it is preferable that both $R^6$ and $R^7$ in $R^x$ and $R^y$ are a hydrogen atom.

$R^1$, $R^2$, $R^3$, $R^4$ and $R^5$ not including $R^y$ each independently represent a hydrogen atom, a substituted or unsubstituted aliphatic group having 1 to 30 carbon atoms, or a sulfonate group. However, $R^1$, $R^2$, $R^3$, $R^4$ and $R^5$ not including $R^y$ are not simultaneously a hydrogen atom.

Preferably, $R^1$, $R^2$, $R^3$, $R^4$ and $R^5$ not including $R^y$ are a substituted or unsubstituted aliphatic group having 1 to 30 carbon atoms.

The number of carbon atoms of the aliphatic group represented by $R^1$, $R^2$, $R^3$, $R^4$ and $R^5$ is preferably 1 to 10, more preferably 1 to 2, from the viewpoint of readily conducting the synthesis, forming a capsule without undergoing steric hindrance among the compounds represented by Formula (I), and preventing the detachment of anion from the capsule.

The aliphatic group may have a substituent, and examples thereof include a halogen atom, a sulfonate group, a nitro group, a hydroxyl group, and a halogenated alkyl group. From the viewpoint of readily conducting the synthesis, or achieving stability and insolubility in water, a fluorine atom or a perfluoroalkyl group is preferable.

In $R^x$ and $R^Y$, the heterocyclic group represented by A may have a substituent such as an alkyl group of 1 to 6 carbon atoms or a sulfonate group. The heterocyclic group may include an oxygen atom or a sulfur atom, in addition to the nitrogen atom.

The heterocyclic group represented by A may be the aforementioned heterocyclic group capable of coordination with a metal ion. Examples of the heterocyclic group include pyrrolyl groups not including a pyrrol-1-yl group, 2H-pyrrolyl groups not including 2H-pyrrol-1-yl group, an imidazolyl group, a pyrazolyl group, isothiazolyl group not including an isothiazol-1-yl group, isoxazolyl groups not including an isoxazol-1-yl group, pyrrolidinyl groups not including a pyrrollidin-1-yl group, an imidazolidinyl group, a pyrazolidinyl group, pyridyl groups not including a pyridin-1-yl group, a pyrazyl group, a pyrimidinyl group, a pyridazinyl group, piperidinyl groups not including a piperidin-1-yl group, a piperazinyl group, morpholinyl groups not including a morpholin-4-yl group, and groups represented by the following structural formulae.

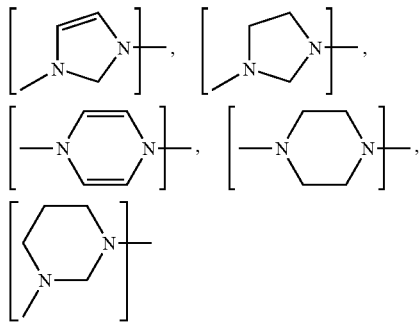

Among the above, from the viewpoint of readily conducting the synthesis and coordination with a metal ion, pyrrolyl groups not including a pyrrol-1-yl group, an imidazolyl group, pyridyl groups not including a pyridine-1-yl group, and groups represented by the following structural formulae are more preferable.

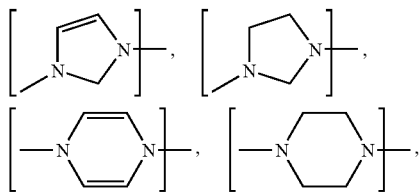

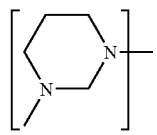

Among the above, an imidazolyl group is particularly preferable.

From the viewpoint of readily conducting the synthesis, inhibiting the generation of isomer, and forming a capsule space from which the trapped molecule does not detach, the heterocycle-substituted aromatic compound represented by Formula (I) is preferably a compound represented by the following Formula (II).

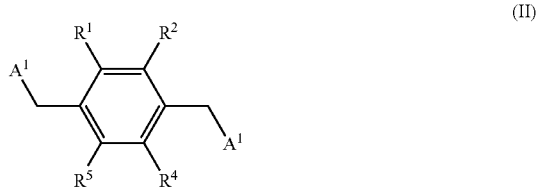

In Formula (II), $R^1$, $R^2$, $R^4$ and $R^5$ have the same definitions as that of $R^1$, $R^2$, $R^4$ and $R^5$ in Formula (I), except that $R^1$, $R^2$, $R^4$ and $R^5$ are not $R^Y$.

Further, in Formula (II), each $A^1$ has the same definition as that of A in Formula (I), and the preferable range is also the same as that of A.

The compound of the invention may be readily synthesized by, for example, reacting an aromatic compound substituted by a halogen with a compound corresponding to A in Formula (I) in the presence of an alkali metal salt, to substitute the halogen atom with A. For example, 1,3-bis(imidazol-1-yl-methyl)benzene may be synthesized by reacting imidazole with α, α'-dibromo-p-xylene in the presence of sodium hydride while heating. Such a synthesis method is described in, for example, C.-H. Zhou, R.-G. Xie, and H.-M. Zhao, Organic Preparations and Procedures Int., 1996, 28(3), 345.

The following are exemplary compounds of the heterocycle-substituted aromatic compound represented by Formula (I) or Formula (II) (exemplary compounds (a) to (g)). However, the invention is not limited thereto.

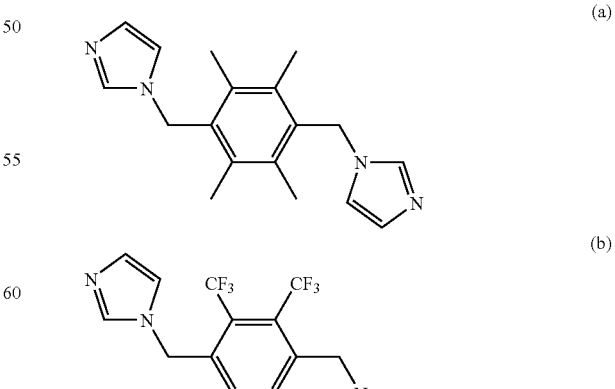

-continued

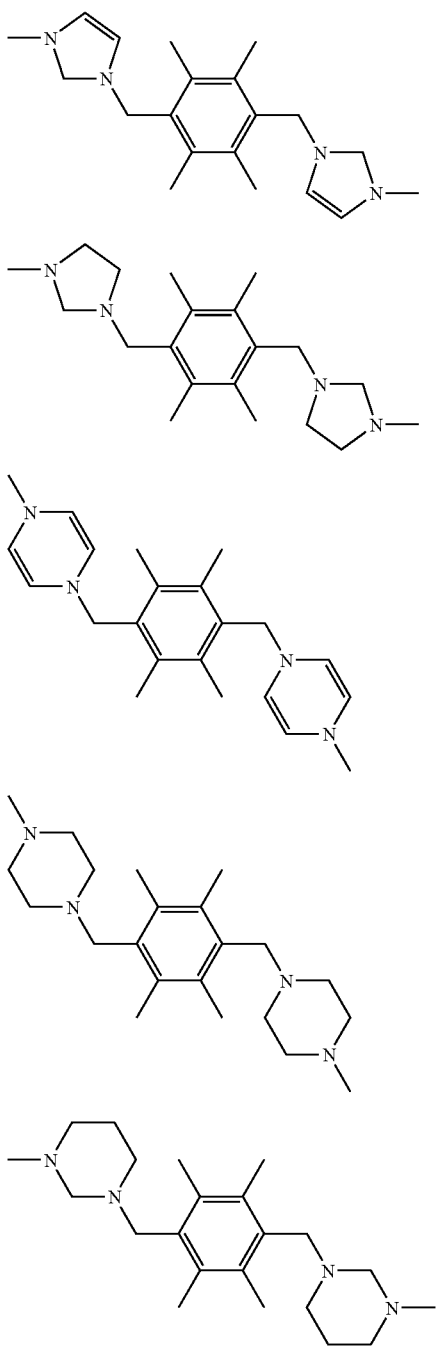

Among the exemplary compounds (a) to (g), exemplary compound (a) or exemplary compound (b) is more preferable.

<Coordination Compound>

The coordination compound of the invention includes the heterocycle-substituted aromatic compound as described above, and a metal ion capable of planar tetra-coordination or octahedral coordination.

When the coordination compound of the invention is brought into contact with a perchlorate ion in a liquid sample, the heterocycle-substituted aromatic compound and the metal ion that compose the coordination compound are reconstituted into a molecular capsule including the perchlorate ion. Therefore, the perchlorate ion can be trapped with high selectivity, as with the case of using the heterocycle-substituted aromatic compound by itself.

One specific structure of the coordination compound of the invention is a polymeric complex structure in which plural aromatic compounds with a heterocyclic substituent coordinate with each of plural metal ions included in the coordination compound.

The structure of the polymeric complex may be, for example, a two-dimensional sheet structure in which four of the aromatic compounds with a heterocyclic substituent coordinate with each metal ion. In the two-dimensional sheet structure, each heterocycle-substituted aromatic compound is positioned between two metal ions, where the aromatic compound coordinates with one of the metal ions at the nitrogen atom in one of the heterocyclic substituent thereof, and coordinates with the other metal ion at the nitrogen atom in the other heterocyclic substituent.

The coordination compound of the invention may include an anion other than the perchlorate ion, as a counter ion of the metal ion. The anion may coordinate with the metal ion (see, for example, FIG. 5 described later) or may not coordinate with the metal ion (see, for example, FIG. 6 described later).

When the structure of the coordination compound is the aforementioned two-dimensional sheet structure including an anion, the anion in the two-dimensional sheet structure may (1) coordinate with a metal ion included in a separate two-dimensional sheet structure, or may (2) form a hydrogen bond with water that is bonding to a metal ion included in a separate two-dimensional sheet structure. In the cases of (1) and (2), the coordination compound has a three-dimensional, layered structure including plural two-dimensional sheet structures.

Examples of the metal ion capable of planar tetra-coordination or octahedral coordination include $Zn^{2+}$, $Cu^{2+}$, $Ni^{2+}$, $Co^{2+}$, $Fe^{2+}$, $Mn^{2+}$, $Ag^+$, $Pd^{2+}$, and $Pt^{2+}$.

Among these, from the viewpoint of forming a coordination compound, $Zn^{2+}$, $Cu^{2+}$, $Ni^{2+}$, $Pd^{2+}$, and $Pt^{2+}$ are preferable, and $Cu^{2+}$ is particularly preferable.

Examples of the anion other than the perchlorate ion, which may be contained in the coordination compound of the invention, include $OH^-$, $SO_4^{2-}$, $CO_3^{2-}$, $NO_3^-$, $CH_3COO^-$, $C_2O_4^{2-}$ $HCOO^-$, $Cl^-$, $Br^-$, $F^-$, $PF_6^-$, acetylacetonate ($C_5H_7O_2^-$), $BF_4^-$, $SiF_6^{2-}$, and $CF_3SO_3^-$.

Among these, from the viewpoint of forming a coordination compound, $NO_3^-$, $SO_4^{2-}$, $OH^-$, and $CO_3^{2-}$ are preferable, and $SO_4^{2-}$ is more preferable.

Methods of synthesizing the coordination compound of the invention include a method of reacting the above metal ion (component A) with the above heterocycle-substituted aromatic compound (component B) at a molar ratio (component A/component B) of 1/2.

The methods of reacting component A with component B include a method including dissolving a metal salt composed of component A and an anion other than perchlorate ion in a solvent (for example, water, dimethylformamide, methanol, ethanol, propanol, acetonitrile, acetone, or the like) to prepare a solution A, dissolving component B in a separate solvent (for example, dimethylformamide, methanol, ethanol, propanol, acetonitrile, acetone, or the like) to prepare a solution B, and mixing and reacting solution A with solution B.

Alternatively, component A and component B may be dissolved in the same solvent and reacted with each other. The solvent used in this case may be a single solvent of methanol, dimethylformamide, ethanol or the like, or may be a mixed solvent of water and acetonitrile, water and dimethylformamide, water and methanol, water and ethanol, methanol and dimethylformamide, ethanol and dimethylformamide, or the like.

<Perchlorate Ion Trapping Agent, Process of Trapping Perchlorate Ion, and Process of Eliminating Perchlorate Ion>

The perchlorate ion trapping agent of the invention includes a heterocycle-substituted aromatic compound represented by Formula (I).

The formulation of the perchlorate ion trapping agent is not particularly limited. For example, the perchlorate ion trapping agent may include the heterocycle-substituted aromatic compound in the form of a powder or a solid such as a tablet. Alternatively, the perchlorate ion trapping agent may be in the form of a mixture of the above solid with other ingredient (a porous solid such as zeolite or activated carbon, or the like). Further, the perchlorate ion trapping agent may be in the form of a solvent in which the solid or the mixture is dissolved or dispersed.

As described above, the heterocycle-substituted aromatic compound represented by Formula (I) forms a molecular capsule, upon contact with the perchlorate ion and the metal ion capable of planar tetra-coordination or octahedral coordination. Therefore, by adding the perchlorate ion trapping agent including the heterocycle-substituted aromatic compound of the invention to a liquid sample, it is possible to trap the perchlorate ion in the liquid sample with high selectivity.

From the viewpoint of contacting the heterocycle-substituted aromatic compound with the metal ion and perchlorate ion in a liquid sample, the perchlorate ion trapping agent of the invention may include a metal ion capable of planar tetra-coordination or octahedral coordination.

Examples of the metal ion capable of planar tetra-coordination or octahedral coordination include ion species similar to the metal ion in the coordination compound described above, and the preferable range is also the same.

The mode of the perchlorate ion trapping agent including the metal ion is not particularly limited, but the following two are preferable.

A first mode is that the perchlorate ion trapping agent of the invention includes the metal ion as a part of the coordination compound. In other words, the perchlorate ion trapping agent of the invention includes the coordination compound. The first mode is preferable in that there is no need of dissolving the metal ion directly in a liquid sample.

A second mode is that the perchlorate ion trapping agent of the invention includes the metal ion as a part of a salt. In other words, the perchlorate ion trapping agent of the invention is in the form of a mixture of the heterocycle-substituted aromatic compound and a metal salt containing the metal ion. The second mode is preferable in that there is no need of synthesizing the coordination compound in advance.

When the perchlorate ion trapping agent of the invention does not include the metal ion, it is possible to contact the heterocycle-substituted aromatic compound with the metal ion and the perchlorate ion by separately adding the perchlorate ion trapping agent and the metal salt including the metal ion to a liquid sample (these may be added simultaneously or at an interval).

Examples of the liquid sample include perchlorate ion-containing aqueous solutions, protonic organic solvents such as methanol and ethanol, and non-protonic organic solvents such as acetone, acetonitrile, and tetrahydrofuran.

Examples of the metal ion capable of planar tetra-coordination or octahedral coordination contained in the metal salt include $Zn^{2+}$, $Cu^{2+}$, $Ni^{2+}$, $Co^{2+}$, $Fe^{2+}$, $Mn^{2+}$, $Ag^+$, $Pd^{2+}$, and $Pt^{2+}$.

Among these, $Zn^{2+}$, $Cu^{2+}$, $Ni^{2+}$, $Pd^{2+}$ and $Pt^{2+}$ are preferable from the viewpoint of forming a stable molecular capsule by means of a strong binding of the heterocyclic group to the metal ion. $Cu^{2+}$ is particularly preferable from the viewpoint of readily forming the molecular capsule.

Examples of the anion contained in the metal salt include $OH^-$, $SO_4^{2-}$, $CO_3^{2-}$, $NO_3^-$, $CH_3COO^-$, $C_2O_4^{2-}$, $HCOO^-$, $Cl^-$, $Br^-$, $F^-$, $PF_6^-$, acetylacetonato ($C_5H_7O_2^-$), $BF_4^-$, $SiF_6^{2-}$, and $CF_3SO_3^-$.

Among the anions described above, $NO_3^-$ is preferable in view of the solubility of the metal salt. In view of the selectivity with respect to the perchlorate ion to be trapped ($ClO_4^-$), $SO_4^{2-}$ is preferable. From the viewpoint of suppressing the contamination of a sample solution, $OH^-$ and $CO_3^{2-}$ are preferable.

In view of the above, the metal salt is particularly preferably $CuSO_4$, $Cu(NO_3)_2$, $Cu(OH)_2$ or $CuCO_3$.

Further, the method of trapping a perchlorate ion of the invention is a method of trapping a perchlorate ion in a liquid sample, the method including a trapping step in which the heterocycle-substituted aromatic compound, the metal ion, and the liquid sample are brought into contact with each other to form a molecular capsule in which the perchlorate ion is trapped.

In the trapping process, the heterocycle-substituted aromatic compound, the metal ion, and the perchlorate ion are brought into contact with each other in a liquid sample, so that these components are able to interact with each other. As a result, a molecular capsule in which one perchlorate ion is included by four heterocycle-substituted aromatic compounds and two metal ions is formed, thereby trapping the perchlorate ion in a reliable manner.

The molecular capsule can trap two more perchlorate ions at the exterior surface (two metal ions) thereof by coordinate bonding, in addition to the perchlorate ion trapped inside thereof. Therefore, one molecular capsule can trap three perchlorate ions. Additionally, it has been confirmed that the molecular capsule can trap one more perchlorate ion in between that and another molecular capsule, in addition to the three perchlorate ions. In other words, it has been found that one molecular capsule can trap up to four perchlorate ions.

The modes as described above can be determined by single crystal structural analysis, visible-ultraviolet spectrometry, or the like.

The method of bringing the heterocycle-substituted aromatic compound, the metal ion, and the perchlorate ion into contact with each other in a liquid sample is not particularly limited.

When the perchlorate ion trapping agent includes the metal ion, applicable methods include a method of adding the perchlorate ion trapping agent to a liquid sample containing a perchlorate ion, and a method of allowing a liquid sample containing the perchlorate ion to go through a filter filled with the perchlorate ion trapping agent.

When the perchlorate ion trapping agent does not include the metal ion, applicable methods include a method of adding the perchlorate ion trapping agent and a metal salt containing the metal ion to a liquid sample (the two components may be added simultaneously or at an interval), and a method of allowing a liquid sample containing the perchlorate ion to go through a filter filled with the perchlorate ion trapping agent and the metal ion.

In the method of trapping a perchlorate ion of the invention, the liquid sample may be heated from the viewpoint of increasing the contact frequency of the heterocycle-substituted aromatic compound, the metal ion and the perchlorate ion in order to improve the reactivity of the formation of molecular capsule. The heating temperature may vary depending on the type of solvent, metal salt, heterocycle-substituted aromatic compound or coordination compound, but is preferably 0 to 100° C., more preferably 20 to 70° C.

When the perchlorate ion trapping agent (and the metal salt, if necessary) is (are) added to the liquid sample, the resulting mixture may be agitated after the addition or may be left to stand without agitation. From the viewpoint of increasing the contact frequency of the perchlorate ion trapping agent, the metal ion and the perchlorate ion in order to improve the reactivity of formation of the molecular capsule, it is preferable to agitate the mixture.

The agitation may be conducted by a method of using an agitator, shaking the container, heating to cause convection, or the like. Among these, the method of shaking the container is preferable.

Since the molecular capsule formed in the trapping step of the method of the invention is trapping a perchlorate ion at a specific ratio, it is possible to determine the quantity of perchlorate ion by determining the quantity of molecular capsule.

Determination of the quantity may be conducted, for example, by a method including re-dissolving the molecular capsule that has precipitated in the solution in acetonitrile or the like to measure its visible-ultraviolet spectrum, and calculating the ratio of the maximum absorption intensity at 540 nm that is identical to the molecular capsule that is trapping the perchlorate ion to the ultraviolet absorption derived from the heterocycle-substituted aromatic compound.

The method of eliminating a perchlorate ion of the invention is a method of eliminating the perchlorate ion from a liquid sample, the method including a trapping step in the aforementioned method of trapping perchlorate ions; and an elimination step of eliminating the molecular capsule from the liquid sample by precipitating the molecular capsule that has been formed in the trapping step.

Since the molecular capsule that has been formed in the trapping step precipitates in the liquid sample, only the perchlorate ion can be readily isolated from the liquid sample.

The isolation can be conducted by a kwon method of separating a precipitate from a solution, such as decantation of supernatant, filtration, or centrifugation.

In the method of eliminating a perchlorate ion of the invention, the molecular capsule that has been eliminated from the liquid sample can be regenerated and recovered in the form of the heterocycle-substituted aromatic compound.

Here, since the molecular capsule has a similar structure to that of general metal complexes, it decomposes in a similar manner to that of general metal complexes to regenerate the heterocycle-substituted aromatic compound.

The regeneration may be conducted by, for example, the following method.

Specifically, the molecular capsule including a perchlorate ion is extracted in an organic solvent such as acetonitrile or methanol. The solution is brought into contact with hydrogen sulfide or the like as a metal precipitator, thereby precipitating a metal sulfide. As the metal precipitator other than hydrogen sulfide, alkali reagents and potassium carbonate which can precipitate a metal as a hydroxide salt or carbonate salt may also be used. Subsequently, the heterocycle-substituted aromatic compound remaining in the solution is collected by concentrating and drying, which is then recrystallized in an organic solvent such as acetonitrile or methanol, thereby regenerating the heterocycle-substituted aromatic compound.

As the method of regenerating the heterocycle-substituted aromatic compound, a method of contacting with an acid such as nitric acid or hydrochloric acid may also be applicable, other than the above method of contacting with a metal precipitator. Specifically, by adding the aforementioned acid to a solution in which the molecular capsule has been extracted, the coordinate bond between the metal ion and the heterocycle-substituted aromatic compound can be cleaved to decompose the molecular capsule. After concentrating and drying the solution in which the molecular capsule has been decomposed, water is added thereto to recover the heterocycle-substituted aromatic compound as a precipitate. Subsequently, the heterocycle-substituted aromatic compound can be recrystallized to regenerate in an organic solvent such as acetonitrile and methanol.

According to the method of eliminating a perchlorate ion of the invention, as described above, the perchlorate ion can be selectively eliminated. Therefore, it is possible to eliminate the perchlorate ion from food or soil at high efficiency by agitating in an aqueous solution together with heterocycle-substituted aromatic compound, not only from liquids such as liquid waste, beverages or milk.

EXAMPLES

In the following, Examples of the present invention are described. However, the invention is not limited thereto.

Example 1

<Synthesis of Exemplary Compound (a) (1,4-bis(imidazol-1-yl-methyl)-2,3,5,6-tetramethylbenzene; bitb)>

Synthesis of Exemplary Compound (a) (bitb) was conducted in accordance with the following Reaction Scheme 1.

First, a THF suspension (5 ml) containing 0.095 g (4 mmol) of NaH (manufactured by Kanto Chemical Co., Ltd.) was gradually added to a THF solution (10 ml) containing 0.33 g (5 mmol) of imidazole (manufactured by Kanto Chemical Co., Ltd.), and the mixture was agitated for 20 minutes. The THF (tetrahydrofuran) used here was a product from Kanto Chemical Co., Ltd., and the same applies to the following.

After the agitation, a THF solution (15 ml) containing 0.64 g (2 mmol) of 1,4-bisbromomethyl-2,3,5,6-tetramethylbenzene (manufactured by Tokyo Chemical Industry Co., Ltd., trivial name: dibromodurene) was gradually added to the solution and the mixture was refluxed at 60° C. for 3 to 5 hours. The solution after the reflux was cooled to ambient temperature, water (40 ml) was added to the solution after cooling, and chloroform (manufactured by Kanto Chemical Co., Ltd.) was further added to extract a crude product. The resulting chloroform extract solution was dried over anhydrous sodium sulfate. The chloroform extract solution after drying was concentrated and petroleum ether (manufactured by Kanto Chemical Co., Ltd.) was added thereto, thereby obtaining Exemplary Compound (a) at a yield of 53%.

Reaction Scheme 1

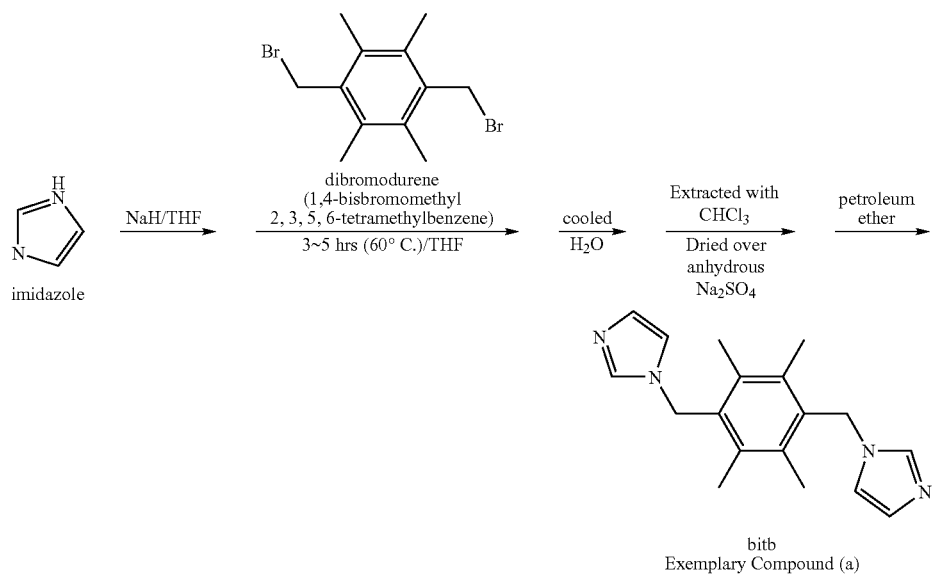

bitb
Exemplary Compound (a)

The structure of Exemplary Compound (a) obtained above was determined by NMR. NMR Data $^1$H NMR spectrum (300 MHz, CDCl$_3$, r.t.): δ 7.24 (d, 2H), 6.97 (s, 2H), 6.75 (d, 2H), 5.17 (s, 4H), 2.19 (s, 12H)

<Synthesis of Exemplary Compound (b)>

Exemplary Compound (b) can be synthesized by a similar method to the above <Synthesis of exemplary compound (a)>, except that 1,4-bis-bromomethyl-2,3,5, 6-tetrakis-trifluoromethylbenzen is used in place of dibromodurene.

Example 2

<Formation of Molecular Capsule Including Perchloric Acid>

0.093 g (0.25 mmol) of copper (II) perchlorate hexahydrate (manufactured by Kishida Chemical Co., Ltd.) and 0.147 g (0.5 mmol) of Exemplary Compound (a) (bitb) obtained in Example 1 were added to a mixed solution of acetonitrile/water (25 ml/25 ml) (the acetonitrile is manufactured by Kanto Chemical Co., Ltd.). The resulting mixed solution was agitated and was then left to stand for several days, thereby obtaining a purple crystal.

The resulting purple crystal was collected, and the structure thereof was determined by single crystal structural analysis and mass spectrometry.

The single crystal structural analysis was conducted by a structure analyzer manufactured by Rigaku Corporation (mercury two-dimensional detector system) using a radiation source of molybdenum Kα to collect X-ray reflection data at ambient temperature. The structural analysis was conducted using the Crystal Structure program manufactured by Rigaku Corporation.

The mass spectrometry was conducted by an LCT mass spectrometer manufactured by Micromass Corporation.

Single Crystal Structural Analysis Data

Monoclinic space group P2$_1$/c(No. 14), a=25.73 (2) Å, b=13.26 (1) Å, c=27.73 (4) Å, β=117.52 (1)°, V=8383 (13) Å$^3$, Z=4, R=0.090, Rw=0.223

Based on the results of single crystal structural analysis data and mass spectrometry, it was determined that the purple crystal was [Cu$_2$(bitb)$_4$](ClO$_4$)$_4$ obtained from the following reaction.

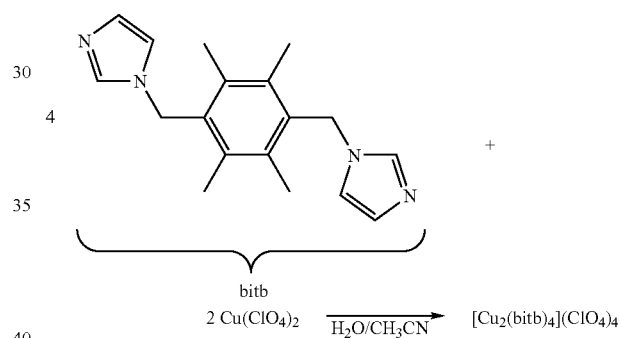

Further, based on the results of single crystal structural analysis data and mass spectrometry, the purple crystal ([Cu$_2$(bitb)$_4$](ClO$_4$)$_4$) was a molecular capsule.

Figure 2:
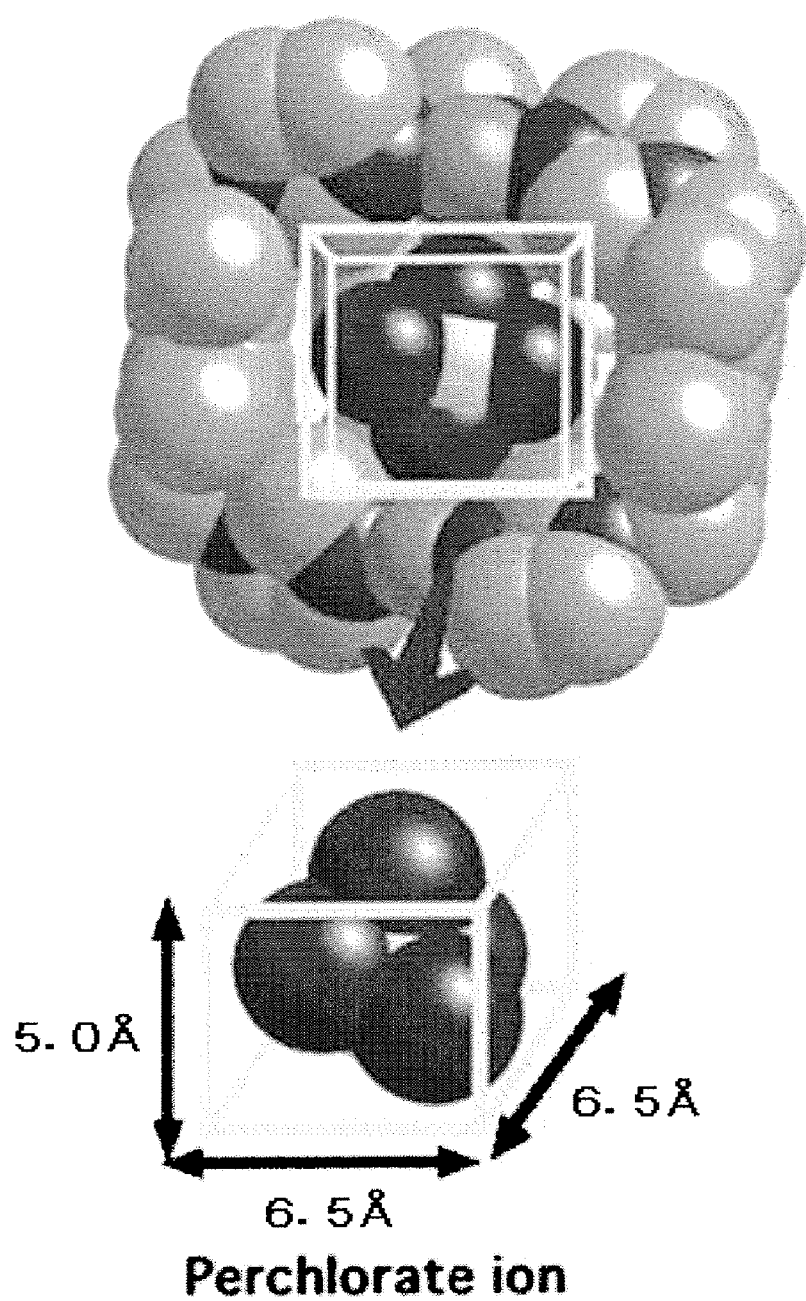
FIG. 2 is an image of the molecular capsule according to the present invention enclosing a molecule of perchlorate ion ($ClO_4^-$) in view of the van der Waals radius.

The structure of molecular capsule that has been clarified by the above single crystal structural analysis data and mass spectrometry is shown in FIGS. 1 and 2.

As shown in FIG. 1, the molecular capsule has a structure in which a capsule backbone formed from two copper (II) ions and four bitb molecules includes one perchlorate ion molecule therein. Although not shown in the drawing, each copper (II) ion is coordinated with one perchlorate ion outside the capsule.

As shown in FIG. 2, the size of the space formed by two copper (II) ions and four bitb molecules was 6.5 angstroms (0.65 nm)×6.5 angstroms (0.65 nm)×5.0 angstroms (0.50 nm), which was able to include the perchlorate ion so as not to release it therefrom.

In FIGS. 1 and 2, hydrogen atoms are not described for the purpose of simplification.

The purple crystal obtained was able to dissolve in any of dimethylformamide, methanol, ethanol, acetonitrile and acetone. This also provides evidence that the purple crystal has a structure of molecular capsule.

Example 3

<Determination of Trapping of Perchloric Acid>

0 to 20 ml of a mixed solution of aqueous sodium perchlorate solution (2.5 mM)/acetonitrile (1:1) was added dropwise to 20 ml of a mixed solution of water/acetonitrile (1:1) containing copper (II) sulfate heptahydrate (5 mM) and bitb (10 mM). The resulting solution was adjusted to 40 ml, and each resulting solution was analyzed by visible-ultraviolet absorption spectrometry to follow the changes.

Herein, a spectrometer of V570 UV-Vis, NIR manufactured by JASCO Corporation was used for visible-ultraviolet absorption spectrometry.

Figure 3:
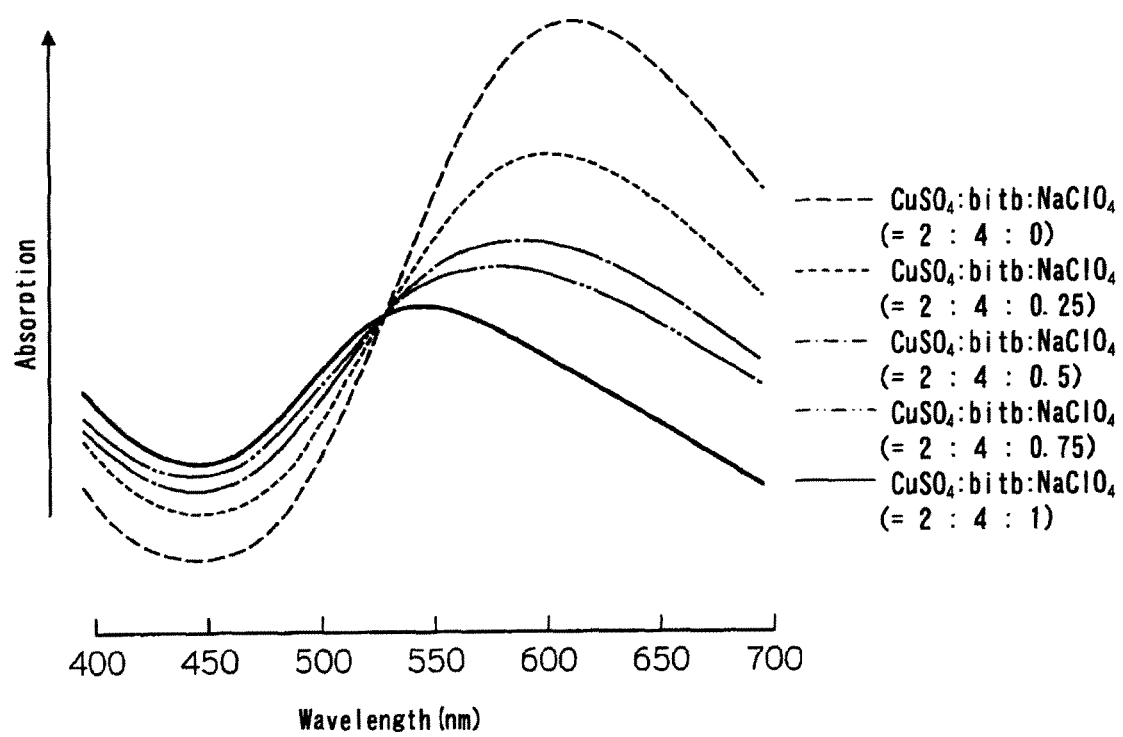
FIG. 3 is a graph showing the changes in visible-ultraviolet absorption spectra observed when an aqueous sodium perchlorate solution was added dropwise to the solution containing copper (II) sulfate heptahydrate and bitb according to the example of the invention.

FIG. 3 shows the visible-ultraviolet absorption spectra observed when a molar ratio of [$CuSO_4$:bitb:$NaClO_4$] is [2:4:0], [2:4:0.25], [2:4:0.5], [2:4:0.75], and [2:4:1].

In FIG. 3, only the absorption spectra in a region of 400 nm to 700 nm, at which a clear change was observed, are shown.

As shown in the graph of FIG. 3, an absorption was observed around 600 nm prior to the instillation of the aqueous sodium perchlorate solution (namely, at a molar ratio of [2:4:0]), but the spectrum changed as the instillation was conducted to increase the molar ratio of sodium perchlorate. When the molar ratio reached [2:4:1], an absorption at 540 nm was newly observed and the absorption spectrum stopped changing. The newly observed absorption at 540 nm corresponded to the absorption of molecular capsule ([$Cu_2(bitb)_4$]($ClO_4$)$_4$), which indicated that a molecular capsule including perchloric acid was generated.

Further, it was verified that an increase in absorption at 540 nm that was specific to the molecular capsule including perchloric acid was observed during the formation of the capsule, suggesting that it is possible to determine the quantity of perchlorate ion using this absorption.

Example 4

<Elimination of Perchloric Acid in Aqueous Solution 1>

Copper sulfate (9.988 mg, 2.0 mmol) and bitb (0.02355 g, 4.0 mmol), both in the form of a solid, were added to 20 ml of an aqueous solution containing 1.0 mmol of sodium perchlorate, and the mixture was sufficiently agitated. After the agitation, insoluble matters that have been generated were removed by filtering, and quantity determination of the remaining perchlorate ion was conducted. The quantity determination was conducted by a conventional method of quantity determination of perchlorate ion. Specifically, an excess amount of a chloride of tris(2,2'-bipyridine) iron (II) complex was added to the filtrate, and ml of nitrobenzene was further added thereto. Because no perchlorate salt of tris(2,2'-bipyridine) iron (II) complex was extracted into nitrobenzene, it was confirmed that the perchlorate salt had been eliminated from the aqueous solution (if perchloric acid remains in the aqueous solution, a perchlorate salt of tris(2,2'-bipyridine) iron (II) complex is generated and extracted into nitrobenzene, which gives a color to the nitrobenzene layer. By measuring the spectrometric spectrum of the colored nitrobenzene layer, quantity determination of perchlorate ion remaining in the aqueous solution can be conducted).

The measurement of spectrometric spectrum was conducted by a spectrometer, V570 UV-Vis. NIR (manufactured by JASCO Corporation).

Example 5

<Elimination of Perchloric Acid in Aqueous Solution 2>

0.049 g (0.2 mmol) of copper (II) sulfate heptahydrate and 0.117 g (0.4 mmol) of bitb were added to each aqueous solution (100 ml) containing sodium perchlorate at respective amounts (0.1 mmol, 0.2 mmol, 0.3 mmol, 0.4 mmol, 0.5 mmol), and the mixture was agitated.

After the agitation, the amount of perchlorate ion remaining in each of the aqueous solutions was determined in the following manner.

Specifically, tris(2,2'-bipyridine) iron (II) complex was added to the aqueous solution after agitation to generate a perchlorate salt [$Fe(bpy)_3$]($ClO_4$)$_2$, which was then extracted in nitrobenzene. Quantity determination of the extracted perchlorate salt was conducted by measuring an absorption at 524 nm of the perchlorate salt. The measurement of absorption was conducted by a spectrometer, V570 UV-Vis. NIR (manufactured by JASCO Corporation).

Figure 4:
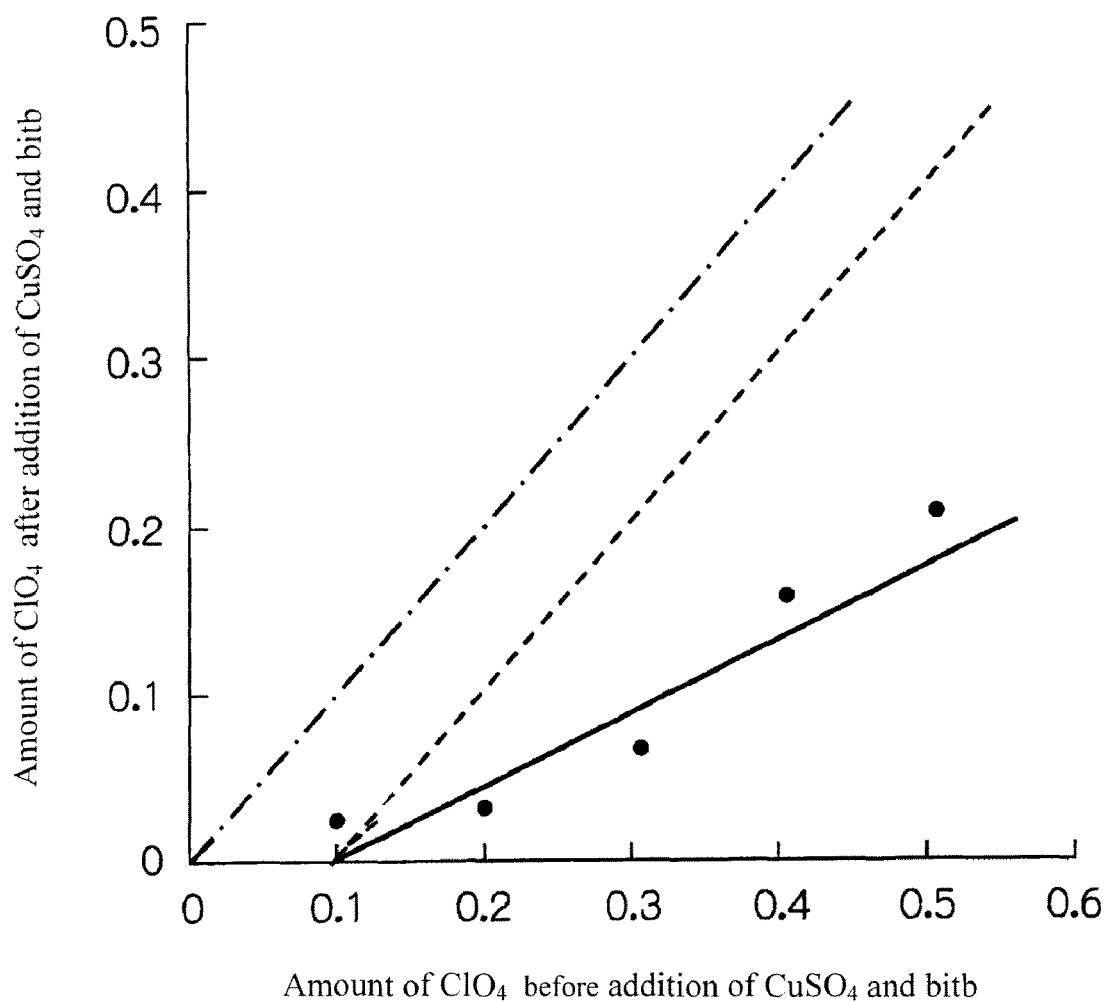
FIG. 4 is a graph showing the amount of perchlorate ion in the aqueous solution containing sodium perchlorate according to the Example of the invention when copper (II) sulfate heptahydrate and bitb were added to the solution.

FIG. 4 shows a graph depicting the amount of perchlorate ion remaining in each of the aqueous solutions.

In FIG. 4, both the transverse axis and the vertical axis indicate the amount of perchlorate ion existing in the aqueous solutions. More specifically, the transverse axis indicates the amount of perchlorate ion before the addition of copper (II) sulfate heptahydrate and bitb, while the vertical axis indicates the amount of perchlorate ion after the addition of copper (II) sulfate heptahydrate and bitb.

In FIG. 4, the chain line represents a theoretical line based on an assumption that two copper (II) ions and four bitb molecules do not trap perchlorate ion at all. In this case, the amount of perchlorate ion in the aqueous solutions does not change by the addition of copper (II) sulfate heptahydrate and bitb, so the chain line is a line with a slope of 1 and an intercept of zero.

In FIG. 4, the dotted line is a theoretical line based on an assumption that two copper (II) ions and four bitb molecules eliminate only one molecule of perchlorate ion. In other words, the dotted line is a line with a slope of 1 and an intercept of −0.1.

In FIG. 4, the plots indicate experimental values of the amount of perchlorate ion after the addition of copper (II) sulfate heptahydrate and bitb, and the solid line is a line estimated from these experimental values.

As apparently shown in FIG. 4, it was verified that two copper (II) ions and four bitb molecules eliminate more than one perchlorate ion molecule.

This is considered to be because one molecular capsule traps a perchlorate ion at the outside of capsule skeleton (position corresponding to metal ion), in addition to the one perchlorate ion trapped inside thereof.

In view of the above, it was confirmed that it is possible to eliminate a perchlorate ion stoichiometrically from a liquid sample, by bringing the heterocycle-substituted aromatic compound (namely, the perchlorate ion trapping agent), the metal ion capable of plane tetra-coordination or octahedral coordination, and the liquid sample into contact, thereby forming and precipitating a molecular capsule.

Example 6

<Synthesis of Coordination Compound Containing Copper (II) Ion and Bitb, and Structure Thereof 1>

Copper sulfate pentahydrate ($CuSO_4 \cdot 5H_2O$, manufactured by Wako Pure Chemical Industries, Ltd.) and dimethylformamide (DMF, manufactured by Kanto Chemical Co., Ltd.) were used as reagents.

58.9 mg (0.2 mmol) of bitb was dissolved in 20 ml of DMF, and 25.0 mg (0.1 mmol) of the copper sulfate was dissolved in 20 ml of water, respectively. The resulting solutions were reacted with each other at one time, and the reaction mixture was left to stand at ambient temperature for one week, thereby recovering a water-insoluble blue crystal.

According to the results of structural analysis, the blue crystal contained seven water molecules as a crystallization solvent per one copper (II) ion molecule. Since the blue crystal did not dissolve in a solvent and was not able to be analyzed by mass spectrometry, the ratio of carbon, hydrogen and nitrogen in the blue crystal was determined by elemental analysis. It was confirmed that the result of elemental analysis corresponded to the result of single crystal structural analysis.

Elemental Analysis Data

Theoretical value ($C_{36}H_{60}CuN_8O_{12}S$) C, 48.45; H, 6.78; N, 12.55

Experimental value C, 48.72; H, 6.41; N, 12.73 (Analyzer: Euro EA3000, manufactured by Euro Vector Co., Ltd)

Single Crystal Structural Analysis Data

Monoclinic space group C2/m (No. 12), $C_{36}H_{60}CuN_8O_{12}S$, Mw (molecular weight) 892.5, a=12.3 (1) Å, b=27.3 (2) Å, c=13.8 (1) Å, β=113.42 (1)°, V=4252 (62) Å$^3$, Z=4, R=0.114, Rw=0.470

The results of the elemental analysis and the single crystal structural analysis showed that the resulting blue crystal was a coordination compound (a polymeric complex represented by $\{[Cu(bitb)_2(H_2O)_2]_\infty[Cu(bitb)_2(SO_4)_2]_\infty\}$), rather than a structure of molecular capsule as obtained in Example 2. Details of the structure of the coordination compound will be described later.

The resulting blue crystal did not dissolve in any of water, dimethylformamide, methanol or ethanol. This result also indicates that the blue crystal had a structure of a coordination compound (a polymeric complex represented by $\{[Cu(bitb)_2(H_2O)_2]_\infty[Cu(bitb)_2(SO_4)_2]_\infty\}$), rather than a structure of molecular capsule.

The reason why the blue crystal had a structure of not molecular capsule but coordination compound is considered to be that the size of sulfate ion is larger than the size of perchlorate ion. Specifically, it is considered to be because the size of a molecule which a capsule backbone composed of four bitb molecules and two metal ions can include does not coincide with the size of sulfate ion, a coordination compound is formed instead of a capsule skeleton.

Figure 5:
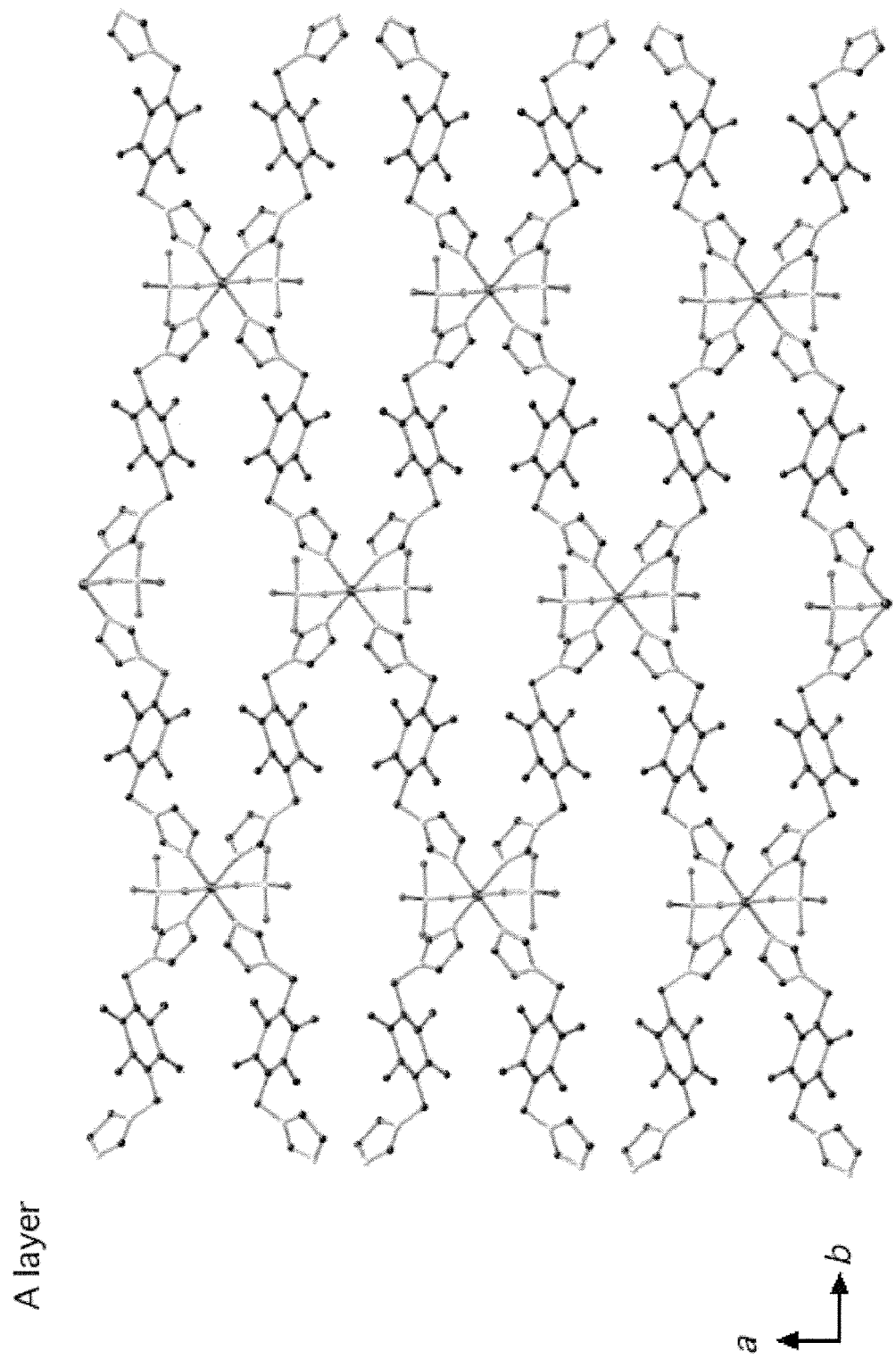
FIG. 5 is a view of the two-dimensional sheet structure (A layer) of the coordination compound according to the Example of the invention.
Figure 6:
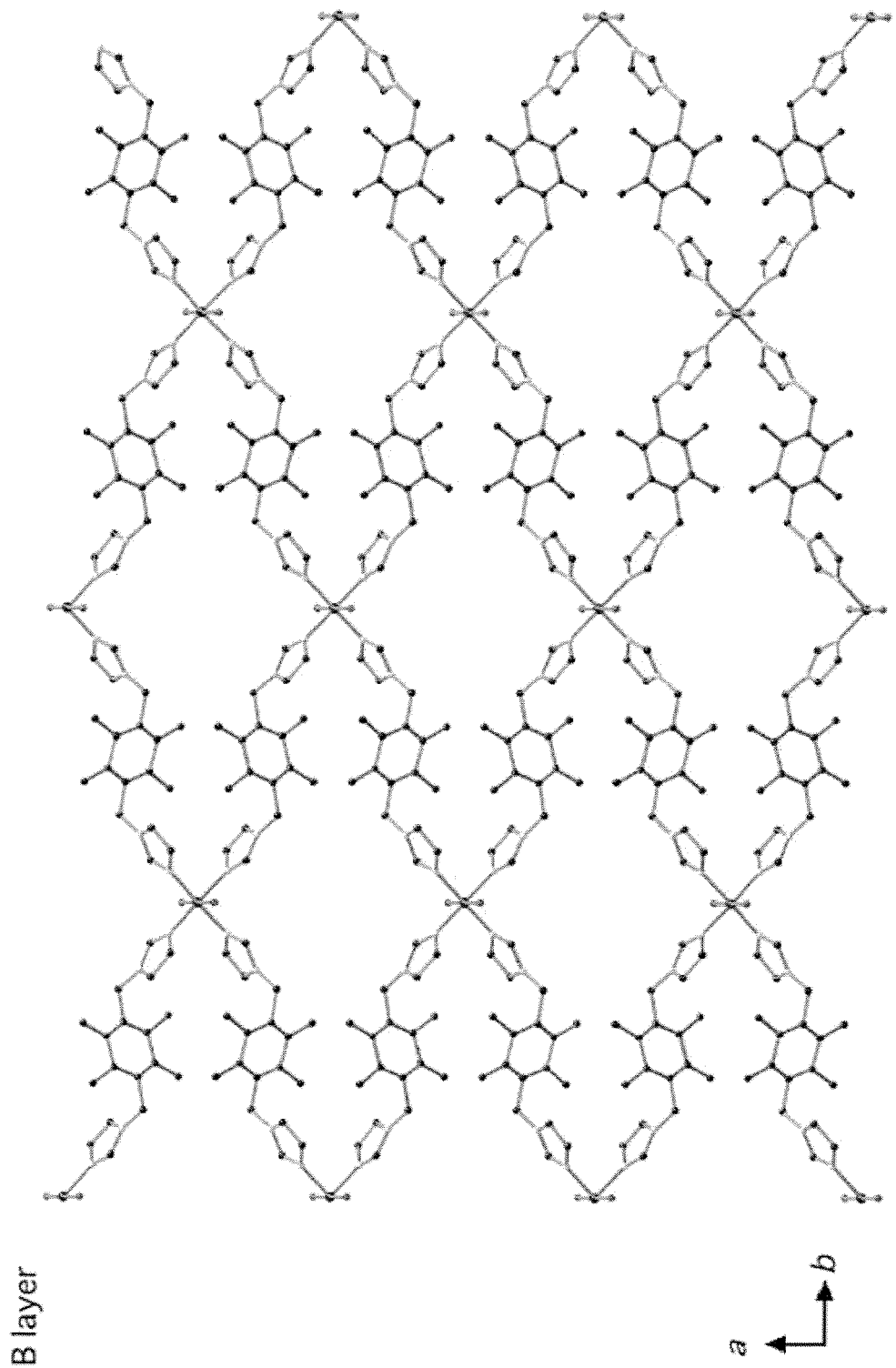
FIG. 6 is a view of the two-dimensional sheet structure (B layer) of the coordination compound according to the Example of the invention.
Figure 7:
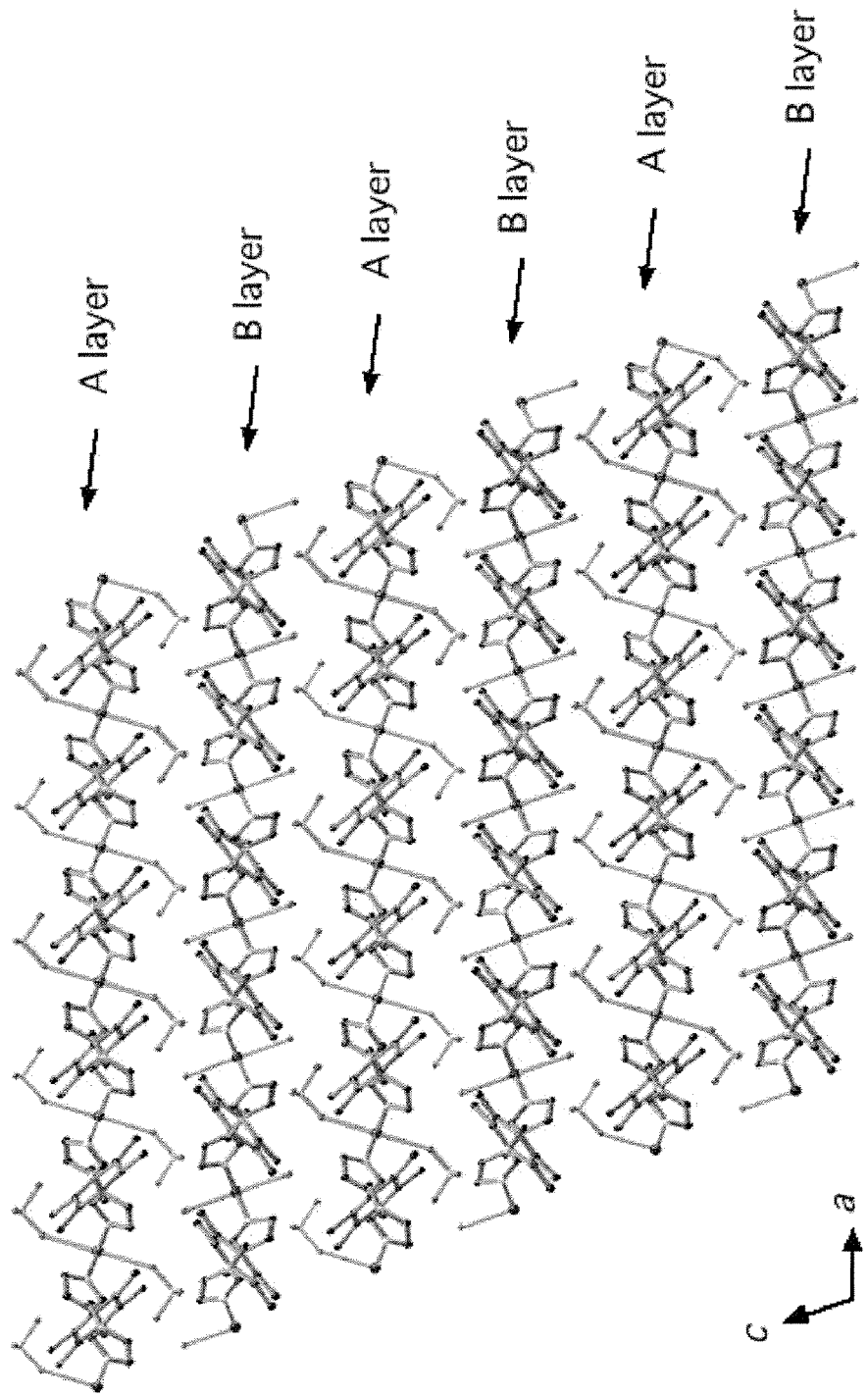
FIG. 7 is a view of the three-dimensional structure of the coordination compound according to the Example of the invention.

The structure of the coordination compound shown by the results of the elemental analysis and the single crystal structural analysis is shown in FIGS. 5 through 7.

In FIGS. 5 and 6, the ion species with six bonds represents copper (II) ion, and the molecule containing one six-membered ring and two five-membered rings (heterocyclic group) that is disposed in between two copper (II) ions represents bitb. Herein, bitb coordinates with one copper (II) ion at a nitrogen atom in one heterocyclic group, and with the other copper (II) ion at a nitrogen atom in the other heterocyclic group. Since the coordination compound has a structure that spreads in the form of an infinite chain, atoms and molecules positioned in the peripheries of the area described in FIGS. 5 through 7 are not shown. Further, in FIGS. 5 through 7, hydrogen atom is not shown for simplification.

As shown in FIGS. 5 to 7, the structure of the coordination compound has a three-dimensional structure (FIG. 7) in which two types of two-dimensional sheet structure (Layer A in FIG. 5 and Layer B in FIG. 6) are alternately layered.

In the following, details of each structure are described.

Layer A shown in FIG. 5 has a two-dimensional sheet structure that spreads two-dimensionally in the form of an infinite chain, in which four bitb molecules coordinate with one copper (II) ion. More specifically, Layer A has a two-dimensional sheet structure $[Cu(bitb)_2(SO_4)_2]_\infty$ with a negative charge, in which two sulfate ion molecules further coordinate with the copper (II) ion. In FIG. 5, arrows "a" and "b" represent axes that are parallel to the two-dimensional plane of Layer A (hereinafter, referred to as "axis a" and "axis b" sometimes).

Layer B shown in FIG. 6 also has a two-dimensional sheet structure that spreads two-dimensionally in the form of an infinite chain, in which four bitb molecules coordinate with one copper (II) ion. More specifically, Layer B has a two-dimensional sheet structure $[Cu(bitb)_2(H_2O)_2]_\infty$ with a positive charge, in which two water molecules further coordinate with the copper (II) ion. In FIG. 6, arrows "a" and "b" represent axes that are parallel to the two-dimensional plane of Layer B (hereinafter, referred to as "axis a" and "axis b" sometimes).

The three-dimensional structure shown in FIG. 7 is a structure in which Layer A and Layer B are alternately layered. In FIG. 7, arrow "c" represents an axis that is not parallel to the two-dimensional planes of Layer A and Layer B. As shown in FIG. 7, Layer A and Layer B are disposed on the "ab" plane, and are alternately layered in a direction of c axis.

In FIG. 7, the sulfate ion coordinating with copper (II) ion in Layer A forms a hydrogen bond with a water molecule coordinating with the copper (II) ion in the adjacent Layer B (O—O=2.98 angstroms). Consequently, a three-dimensional structure is formed via a hydrogen bond.

Example 7

<Synthesis and Structure of Coordination Compound Containing Copper (II) Ion and bitb 2>

The same procedures as conducted in Example 2 were carried out to obtain a water-insoluble blue crystal, except that 0.093 g (0.25 mmol) of copper (II) perchlorate hexahydrate (manufactured by Kishida Chemical Co., Ltd.) was changed to 0.062 g (0.025 mmol) of copper (II) sulfate heptahydrate (manufactured by Wako Pure Chemical Industries, Ltd.). The blue crystal was collected and crystal structural analysis was conducted to determine a unit cell. It was confirmed that a polymeric coordination compound represented by $\{[Cu(bitb)_2(H_2O)_2]_\infty[Cu(bitb)_2(SO_4)_2]_\infty\}$ as synthesized in Example 6 was obtained.

Single Crystal Structural Analysis Data a=12.4 (3) Å, b=27.4 (7) Å, c=13.8 (3) Å, β=113.6 (1)°

Example 8

<Synthesis and Structure of Coordination Compound Containing Copper (II) Ion and bitb 3>

The same procedure as conducted in Example 6 were carried out, except that a copper (II) ion having an anion such as a nitrate, chloride, carbonate, acetate or hydroxide was used as a starting material in place of copper sulfate pentahydrate ($CuSO_4 \cdot 5H_2O$). An insoluble Cu-bitb coordination compound was obtained at a yield of 30% or more, as with the case in Example 6.

Since the resulting Cu-bitb coordination compound also exhibited a low solubility to water, dimethylformamide, methanol or ethanol, it is considered that the compound has a polymeric structure.

Example 9

<Trapping of Perchloric Acid by Coordination Compound Containing Copper (II) Ion and bitb>

A trapping experiment of perchloric acid was executed using the coordination compound synthesized in Example 6, $\{[Cu(bitb)_2(H_2O)_2]_\infty[Cu(bitb)_2(SO_4)_2]_\infty\}$ (hereinafter, referred to as "Cu-bitb coordination compound A") as the coordination compound containing copper (II) ion and bitb.

Specifically, a 0.5 mM sodium perchlorate aqueous solution was prepared. To 10 ml of the obtained aqueous solution was added 29.95 mg (0.02 mmol) of a Cu-bitb coordination compound (A), which was of 2-fold equivalent of perchlorate ion calculated based on the molar number of the contained copper (II) ion. The resulting mixture was left to stand for 6 hours for reaction, to obtain a reaction solution 1.

In the solution, a blue precipitate that was considered to be Cu-bitb coordination compound (A) was observed immediately after the addition of Cu-bitb coordination compound (A), but the precipitate turned purple 6 hours after the addition.

The change in color of the precipitate is considered to be due to the change in the precipitate from Cu-bitb coordination compound (A) to a molecular capsule $\{[Cu_2(bitb)_4](ClO_4)_4\}$.

The reflection spectrum of the blue precipitate 1.5 hours after the addition of Cu-bitb coordination compound (A) and the reflection spectrum of the purple precipitate 6 hours after the addition of the Cu-bitb coordination compound (A) were determined, respectively. The results are shown in FIG. 8.

Figure 8:
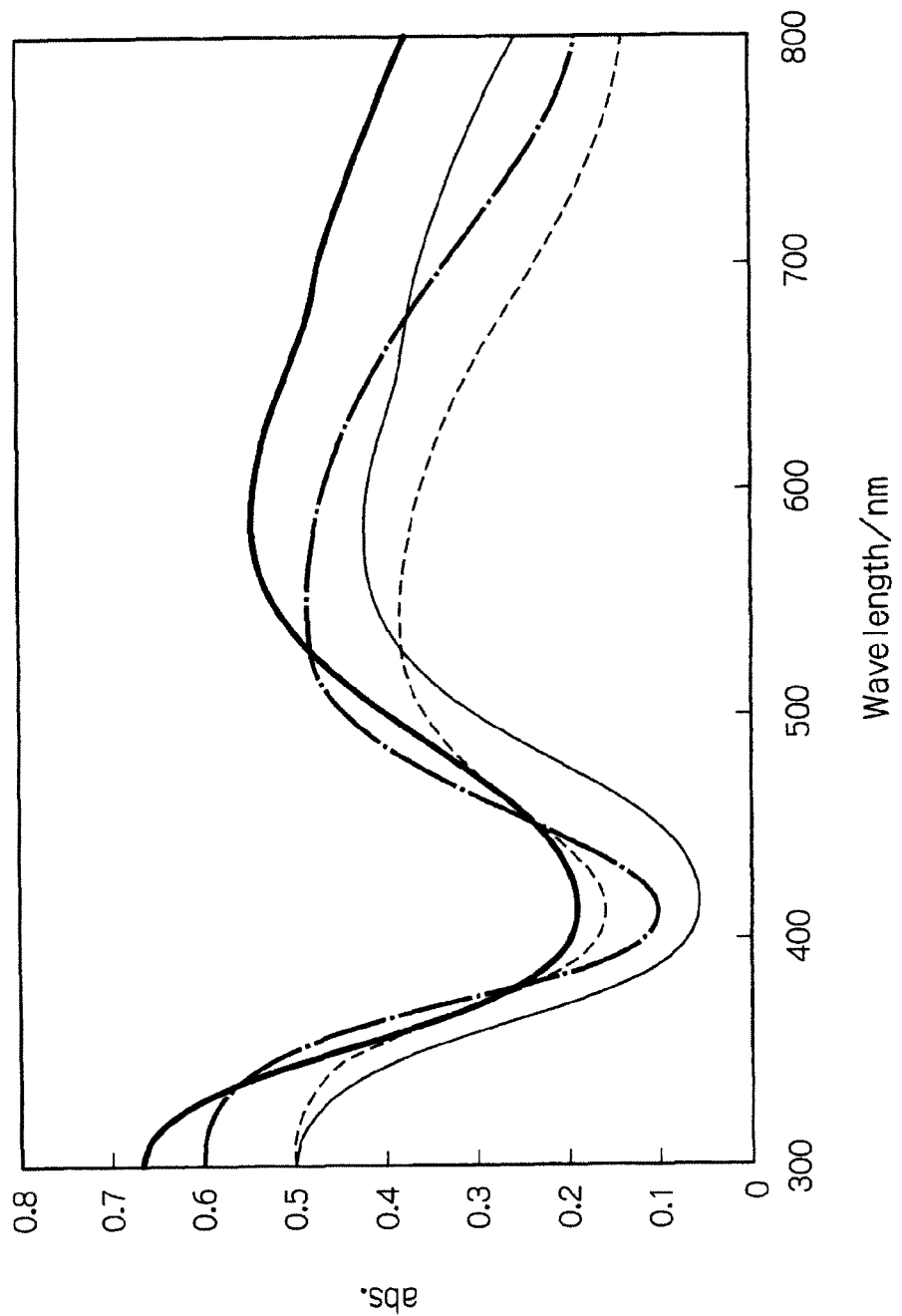
FIG. 8 is a reflection spectra observed when the coordination compound according to the Example of the invention was added to an aqueous sodium perchlorate solution.

In FIG. 8, the bold solid line represents a reflection spectrum of the blue precipitate 1.5 hours after the addition of Cu-bitb coordination compound (A), while the bold chain line represents a reflection spectrum of the purple precipitate 6 hours after the addition of the Cu-bitb coordination compound (A). Further, the thin solid line represents a reflection spectrum of Cu-bitb coordination compound (A), while the thin dashed line represents a reflection spectrum of a molecular capsule $[Cu_2(bitb)_4](ClO_4)_4$.

As apparently shown in FIG. 8, the absorption spectrum of the blue precipitate 1.5 hours after the addition had an absorption peak at around 590 nm, which corresponded to the reflection spectrum of Cu-bitb coordination compound (A). On the other hand, the absorption spectrum of the purple precipitate 6 hours after the addition had an absorption peak at around 540 nm, which corresponded to the reflection spectrum of the molecular capsule $[Cu_2(bitb)_4](ClO_4)_4]$.

As described above, it was confirmed that Cu-bitb coordination compound (A) changed it structure to the molecular capsule $\{[Cu_2(bitb)_4](ClO_4)_4\}$ within 6 hours after the contact with perchlorate ion.

In other words, it was confirmed that the copper (II) ion and bitb that had been generated from Cu-bitb coordination compound (A) trapped the perchlorate ion, thereby forming the molecular capsule.

Example 10

<Elimination of Perchloric Acid by Coordination Compound Containing Copper (II) Ion and Bitb>

A trapping experiment of perchloric acid was conducted in the following manner, using Cu-bitb coordination compound (A) as a coordination compound containing copper (II) ion and bitb.

Reaction solution 1 obtained in Example 9 was filtered to remove the purple precipitate. To the resulting filtrate was added 1.55 mg (2.5 μmol) of tris(2,2'-bipyridine) iron (II) complex, which was of 0.5-fold equivalent of perchlorate ion, and 10 ml of nitrobenzene was further added to extract iron (II) complex $[Fe(bpy)_3](ClO_4)_2$. The absorption spectrum of Fe(II) complex $[Fe(bpy)_3](ClO_4)_2$ extracted in nitrobenzene was analyzed.

Separately, 10 ml of a 0.5 mM sodium perchlorate aqueous solution to which Cu-bitb coordination compound (A) was not added was prepared as a blank solution. The same procedure as conducted in reaction solution 1 were carried out using the blank solution to determine the absorption spectrum of iron (II) complex $[Fe(bpy)_3](ClO_4)_2$.

Based on the intensity of peak absorption derived from iron (II) complex $[Fe(bpy)_3](ClO_4)_2$ (absorption wavelength: 524 nm) among the absorption spectrum of reaction solution 1 and the absorption spectrum of the blank solution, the concentration of perchlorate ion (concentration of iron (II) complex $[Fe(bpy)_3](ClO_4)_2$) was estimated.

Further, the elimination efficiency (%) of perchlorate ion was determined according to the following equation 1.

Efficiency elimination of perchlorate ion (%)=((concentration of perchlorate ion in blank solution−concentration of perchlorate ion in reaction solution 1)/(concentration of perchlorate ion in blank solution))×100     Equation 1

Next, as a control experiment, an experiment of eliminating perchloric acid was conducted by a method in which copper sulfate (copper (II) ion) and bitb were separately added.

Specifically, filtration, extraction and absorption spectrum analysis were conducted in a similar manner as in Example 9, except that 4.99 mg (0.02 mmol) of copper sulfate and 11.78 mg (0.04 mmol) of bitb were added to 10 ml of 0.5 mM sodium perchlorate aqueous solution, in place of 29.95 mg (0.02 mmol) of Cu-bitb coordination compound (A), and the elimination efficiency of perchlorate ion was determined.

Figure 9:
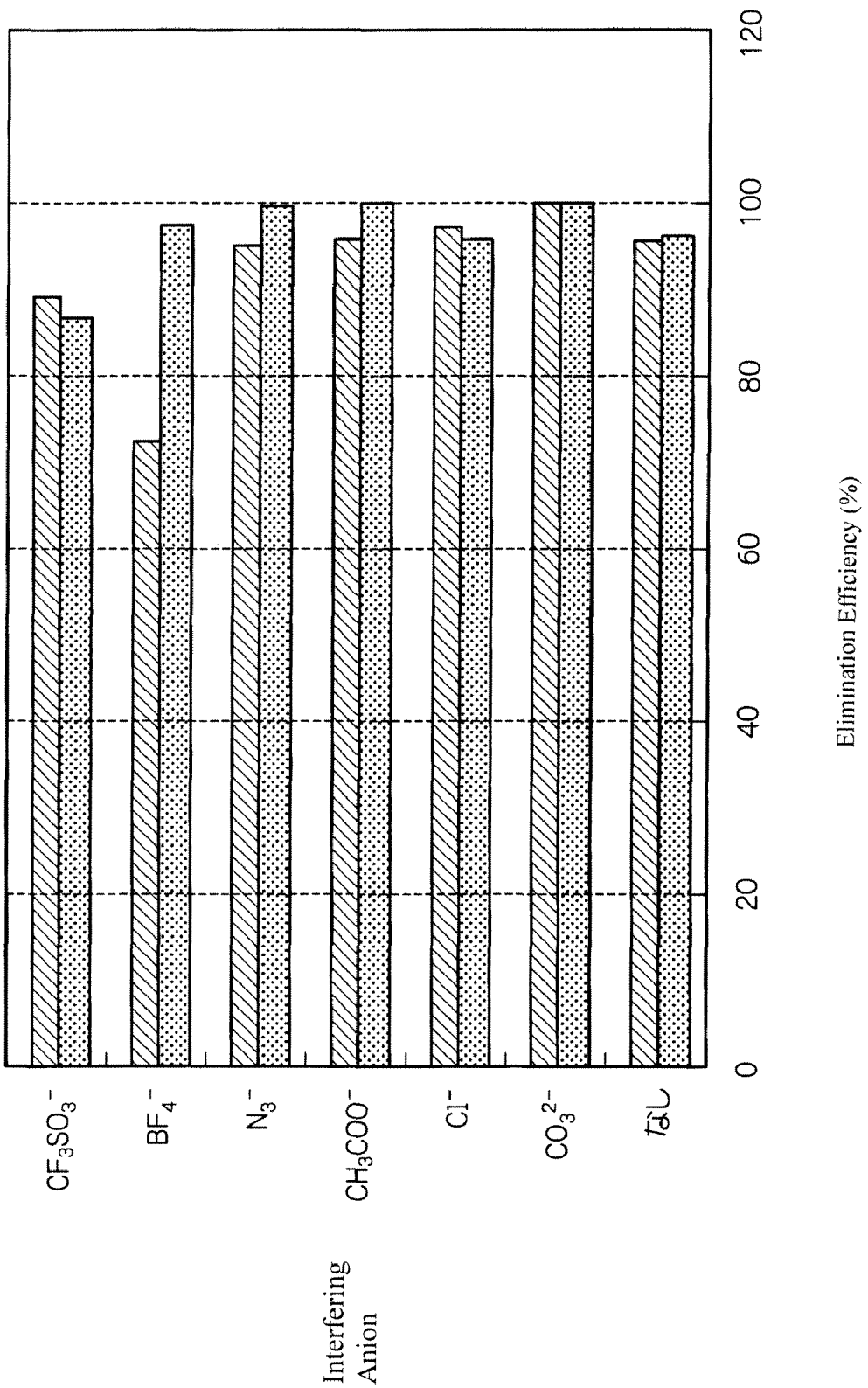
FIG. 9 is a graph showing the elimination efficiency of perchlorate ion according to the Example of the invention.

The result is shown in the column indicated as "none" in Table 1. Further, the data in Table 1 is graphically shown in the column "none" in FIG. 9. In FIG. 9, bars with a hatched pattern (upper) show the elimination efficiency in the method of using a coordination compound containing copper (II) ion and bitb (Cu-bitb coordination compound (A)), while bars (lower) with a dotted pattern show the elimination efficiency in the method of separately adding copper sulfate (copper (II) ion) and bitb.

As shown in Table 1 and FIG. 9, the results of the case in which the coordination compound containing copper (II) ion and bitb were used (elimination efficiency: 95.51%) and the results of the case in which copper sulfate (copper (II) ion) and bitb were separately added (elimination efficiency: 95.91%) are almost identical, indicating that the elimination of perchlorate ion is progressing.

Subsequently, 10 ml of 0.5 mM sodium perchlorate aqueous solutions each containing carbonate ion ($CO_3^{2-}$), chloride ion ($Cl^-$), acetate ion ($CH_3COO^-$), azide ion ($N_3^-$), tetrafluoroborate ion ($BF_4^-$) and trifluoromethanesulfonate ion ($CF_3SO_3^-$) as an interfering anion were prepared. Using the resulting solutions, elimination of perchloric acid by a coordination compound containing copper (II) ion and bitb and elimination of perchloric acid by separately adding copper sulfate (copper (II) ion) and bitb were experimented by the method as described above.

Herein, the interfering anion was mixed in the solution in the form of a sodium salt. Further, the ratio of perchlorate ion and interfering anion was adjusted to 1:1 in molar ratio.

The results are shown in Table 1 and FIG. 9. In FIG. 9, bars with a hatched pattern (upper) show the elimination efficiency in the method of using the coordination compound containing copper (II) ion and bitb (Cu-bitb coordination compound (A)), while bars with a dotted pattern (lower) show the elimination efficiency in the method of separately adding copper sulfate (copper (II) ion) and bitb.

TABLE 1

| Interfering anion | Elimination efficiency when copper (II) ion and bitb are separately added (%) | Elimination efficiency when coordination compound containing copper (II) ion and bitb is added (%) |
| --- | --- | --- |
| None | 95.91 | 95.51 |
| $CO_3^{2-}$ | 99.94 | 99.88 |
| $Cl^-$ | 95.41 | 97.11 |
| $CH_3COO^-$) | 99.60 | 95.46 |
| $N_3^-$ | 99.17 | 94.87 |
| $BF_4^-$ | 97.48 | 71.87 |
| $CF_3SO_3^-$ | 86.45 | 88.69 |

As shown in Table 1 and FIG. 9, similar results to that obtained when no interfering anion was present were obtained even in the presence of the interfering anion. Consequently, it is apparent that perchloric acid can be selectively precipitated and eliminated by either way of separately adding copper (II) ion and bitb, or adding a coordination compound containing copper (II) ion and bitb.

The disclosure of JP-A No. 2006-241297 is incorporated in its entirety by reference in the present specification.

All the references, the patent applications and the technical standards described in the specification are incorporated by reference in the specification at the same extents as in the cases where the individual references, the individual patent applications and the individual technical standards are specifically and individually described.

The invention claimed is:

1. A heterocycle-substituted aromatic compound represented by the following Formula (a):

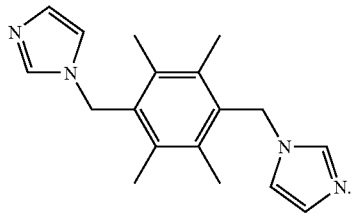

(a)

2. A coordination compound comprising the heterocycle-substituted aromatic compound according to claim 1, and a metal ion capable of planar tetra-coordination or octahedral coordination.

3. The coordination compound according to claim 2, wherein the metal ion is at least one of $Zn^{2+}$, $Cu^{2+}$, $Ni^{2+}$, $Co^{2+}$, $Fe^{2+}$, $Mn^{2+}$, $Ag^+$, $Pd^{2+}$, or $Pt^{2+}$.

4. A perchlorate ion trapping agent comprising a heterocycle-substituted aromatic compound represented by the following formula (a):

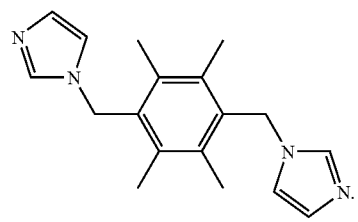

(a)

5. The perchlorate ion trapping agent according to claim 4, further comprising a metal ion capable of planar tetra-coordination or octahedral coordination.

6. The perchlorate ion trapping agent according to claim 5, wherein the metal ion is included as a part of a salt.

7. The perchlorate ion trapping agent according to claim 5, wherein the metal ion is at least one of $Zn^{2+}$, $Cu^{2+}$, $Ni^{2+}$, $Co^{2+}$, $Fe^{2+}$, $Mn^{2+}$, $Ag^+$, $Pd^{2+}$, or $Pt^{2+}$.

8. A method of trapping a perchlorate ion in a liquid sample, comprising a trapping step of bringing the heterocycle-substituted aromatic compound according to claim 1, a metal ion capable of planar tetra-coordination or octahedral coordination, and the liquid sample into contact with each other to form a molecular capsule in which a perchlorate ion is trapped.

9. A method of eliminating a perchlorate ion from a liquid sample, comprising:
 a trapping step of bringing the heterocycle-substituted aromatic compound according to claim 1, a metal ion capable of planar tetra-coordination or octahedral coordination, and the liquid sample into contact with each other to form a molecular capsule in which a perchlorate ion is trapped; and
 an elimination step of precipitating and eliminating the molecular capsule from the liquid sample.

10. The method of trapping a perchlorate ion in a liquid sample according to claim 8, wherein the metal ion is included as a part of a salt.

11. The method of trapping a perchlorate ion in a liquid sample according to claim 8, wherein the metal ion is at least one of $Zn^{2+}$, $Cu^{2+}$, $Ni^{2+}$, $Co^{2+}$, $Fe^{2+}$, $Mn^{2+}$, $Ag^+$, $Pd^{2+}$, or $Pt^{2+}$.

12. The method of eliminating a perchlorate ion from a liquid sample according to claim 9, wherein the metal ion is included as a part of a salt.

13. The method of eliminating a perchlorate ion from a liquid sample according to claim 9, wherein the metal ion is at least one of $Zn^{2+}$, $Cu^{2+}$, $Ni^{2+}$, $Co^{2+}$, $Fe^{2+}$, $Mn^{2+}$, $Ag^+$, $Pd^{2+}$, or $Pt^{2+}$.

* * * * *